(12) United States Patent
Shariat-Madar et al.

(10) Patent No.: US 9,193,762 B2
(45) Date of Patent: Nov. 24, 2015

(54) SELECTIVE INHIBITORS OF PROLYLCARBOXYPEPTIDASE

(75) Inventors: Ziaeddin Shariat-Madar, Oxford, MS (US); John Matthew Rimoldi, Oxford, MS (US); Rama Sarma Venkata Subbarahmanya Gadepalli, Oxford, MS (US)

(73) Assignee: UNIVERSITY OF MISSISSIPPI, University, MS (US)

( * ) Notice: Subject to any disclaimer, the term of this patent is extended or adjusted under 35 U.S.C. 154(b) by 73 days.

(21) Appl. No.: 13/991,094

(22) PCT Filed: Dec. 1, 2011

(86) PCT No.: PCT/US2011/062889
§ 371 (c)(1),
(2), (4) Date: Aug. 6, 2013

(87) PCT Pub. No.: WO2012/075287
PCT Pub. Date: Jun. 7, 2012

(65) Prior Publication Data
US 2013/0310311 A1    Nov. 21, 2013

Related U.S. Application Data

(60) Provisional application No. 61/418,708, filed on Dec. 1, 2010.

(51) Int. Cl.
| C07K 5/078 | (2006.01) |
|---|---|
| C07D 403/06 | (2006.01) |
| C07D 205/04 | (2006.01) |
| C07D 207/16 | (2006.01) |
| C07K 5/02 | (2006.01) |

(52) U.S. Cl.
CPC .......... *C07K 5/06165* (2013.01); *C07D 205/04* (2013.01); *C07D 207/16* (2013.01); *C07D 403/06* (2013.01); *C07K 5/0205* (2013.01); *C07K 5/06139* (2013.01)

(58) Field of Classification Search
None
See application file for complete search history.

(56) References Cited

U.S. PATENT DOCUMENTS

| 5,602,253 | A | 2/1997 | Antonsson et al. |
|---|---|---|---|
| 6,809,108 | B1 | 10/2004 | Sagara et al. |
| 2008/0194485 | A1 * | 8/2008 | Horvath et al. ................ 514/14 |

OTHER PUBLICATIONS

Zhou et al. J. Med. Chem., 2010, vol. 53, pp. 7251-7263.*
International Search Report mailed on Nov. 9, 2012, for PCT/US2011/062889.

(Continued)

*Primary Examiner* — James D Anderson
(74) *Attorney, Agent, or Firm* — Hershkovitz & Assoc., PLLC; Abraham Hershkovitz; Eugene C. Rzucidlo

(57) ABSTRACT

The present invention relates to compounds of the formulae:

in which R is $C_5$-$C_{16}$ alkyl, $R_1$ is and isosteres and salts thereof.

5 Claims, 22 Drawing Sheets

(56) References Cited

OTHER PUBLICATIONS

Written Opinion of the International Search Report mailed on Nov. 9, 2012, for PCT/US2011/062889.

International Preliminary Report on Patentability issued on Jun. 4, 2013, for PCT/US2011/062889.

* cited by examiner

Figure 1A    Synthesis of Z-Pro-Pro-NH amides and PRCP inhibition data

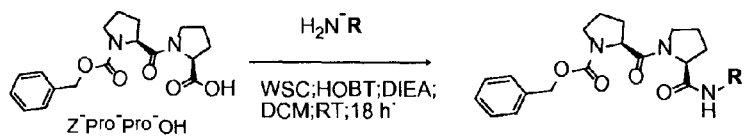

Scheme 1

Table 1.

| Compound Number | R | Mol. Formula | Analyses H¹NMR | Analyses MS | rPRCP Ki (µM) | PRCP-dependent PK activation on HPAEC KI (µM) |
|---|---|---|---|---|---|---|
| RS-33-1 | (benzyl) | $C_{25}H_{29}N_3O_4$ | √ | √ | 338.4 | NE |
| RS-33-2 | (3,4-dichlorobenzyl) | $C_{25}H_{27}Cl_2N_3O_4$ | √ | √ | 80.6 | NE |
| RS-33-3 | (4-chlorophenethyl) | $C_{26}H_{30}Cl_1N_3O_4$ | √ | √ | 160 | NE |
| RS-33-4 | (2-methoxybenzyl) | $C_{27}H_{33}N_3O_5$ | √ | √ | 424.6 | NE |
| RS-33-5 | (alkyl chain) | $C_{28}H_{43}N_3O_4$ | √ | √ | NE | NE |
| RS-33-6 | (long alkyl chain) | $C_{34}H_{55}N_3O_4$ | √ | √ | 61 | 141.4 |
| RS-33-7 | (alkyl chain) | $C_{33}H_{53}N_3O_4$ | √ | √ | 61.5 | 64.2 |
| RS-33-8 | (CF₃/OCH₃ phenyl) | $C_{26}H_{28}F_3N_3O_5$ | √ | √ | NE | NE |
| RS-33-9 | (2-chlorobenzyl) | $C_{25}H_{28}Cl_1N_3O_4$ | √ | √ | 203.1 | NE |
| RS-33-10 | (2,4-dichlorobenzyl) | $C_{25}H_{27}Cl_2N_3O_4$ | √ | √ | NE | 192.9 |

Figure 1B
| | | | | | | |
|---|---|---|---|---|---|---|
| RS-33-11 |  | $C_{26}H_{28}F_3N_3O_4$ | √ | √ | 135.4 | 488.6 |
| RS-33-12 |  | $C_{25}H_{28}Cl_1N_3O_4$ | √ | √ | 264.6 | 257.1 |
| RS-33-13 |  | $C_{25}H_{27}F_2N_3O_4$ | √ | √ | 541.5 | 835.7 |
| RS-33-14 |  | $C_{25}H_{28}Cl_1N_3O_4$ | √ | √ | 467.7 | 900 |
| RS-33-15 |  | $C_{26}H_{31}N_3O_5$ | √ | √ | 289.2 | 771.4 |
| RS-33-16 |  | $C_{26}H_{31}N_3O_5$ | √ | √ | 393.8 | 450 |
| RS-33-17 |  | $C_{26}H_{30}Br_1N_3O_4$ | √ | √ | 110.8 | 282.9 |
| RS-33-18 |  | $C_{23}H_{33}N_3O_4$ | √ | √ | 289.2 | 565.7 |
| RS-33-19 |  | $C_{25}H_{37}N_3O_4$ | √ | √ | 80 | 437.1 |
| RS-33-20 |  | $C_{30}H_{47}N_3O_4$ | √ | √ | 61.5 | 64.3 |
| RS-33-22 |  | $C_{27}H_{41}N_3O_7$ | √ | √ | NE | NE |
| RS-33-23 |  | $C_{26}H_{29}N_3O_6$ | √ | √ | NE | NE |
| RS-33-24 |  | $C_{27}H_{33}N_3O_4$ | √ | √ | NE | NE |
| RS-33-25 |  | $C_{28}H_{37}N_3O_4$ | √ | √ | NE | NE |
| RS-33-27 |  | $C_{30}H_{31}N_3O_4$ | √ | √ | NE | NE |
| RS-33-28 |  | $C_{28}H_{29}N_3O_4$ | √ | √ | NE | NE |
| RS-33-29 |  | $C_{26}H_{31}Cl_1N_3O_6$ | √ | √ | NE | NE |

Synthesis of NH-Pro-Pro-NH amides and PRCP inhibition data

Scheme 2

Table 2.

| Compound Number | R | Mol. Formula | Analyses H¹NMR MS | | rPRCP Ki (μM) | PRCP-dependent PK activation on HPAEC Ki (μM) |
|---|---|---|---|---|---|---|
| RS-33-12a | | $C_{17}H_{22}Cl_1N_3O_2$ | | √ | NE | NE |
| RS-33-13a | | $C_{17}H_{21}F_2N_3O_2$ | √ | √ | NE | NE |
| RS-33-21 | | $C_{22}H_{41}N_3O_2$ | √ | √ | 43.1 | 34.1 |
| RS-33-23a | | $C_{18}H_{23}N_3O_4$ | √ | √ | NE | NE |
| RS-33-26 | | $C_{20}H_{31}N_3O_2$ | | √ | NE | NE |
| RS-33-27a | | $C_{22}H_{25}N_3O_2$ | √ | √ | NE | NE |
| RS-33-28a | | $C_{20}H_{23}N_3O_2$ | √ | √ | NE | NE |
| RS-33-29a | | $C_{18}H_{25}N_3O_4$ | | √ | NE | NE |

Fig. 3
Synthesis of N-R-Pro-Pro-NH dodecylamides and PRCP inhibition data
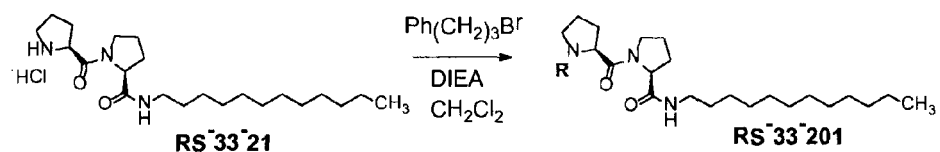
Scheme 3
Table 3.
| Compound Number | R | Mol. Formula | Analyses H$^1$NMR   MS | rPRCP Ki (µM) | PRCP-dependent PK activation on HPAEC Ki (µM) |
|---|---|---|---|---|---|
| RS-33-201 |  | C$_{31}$H$_{51}$N$_3$O$_2$ | √   √ | NE | NE |

Synthesis of N-R-Pro-Pro-NH dodecylamides and PRCP inhibition data

Scheme 4

Table 4.

| Compound Number | R | Mol. Formula | Analyses H¹NMR MS | | rPRCP Ki (µM) | PRCP-dependent PK activation on HPAEC Ki (µM) |
|---|---|---|---|---|---|---|
| RS-40-1 | (phenyl-CH2) | $C_{29}H_{47}N_3O_2$ | √ | √ | NE | NE |
| RS-40-2 | (4-pyridyl-CH2) | $C_{28}H_{46}N_4O_2$ | √ | √ | NE | NE |
| RS-40-3 | (3-pyridyl-CH2) | $C_{28}H_{46}N_4O_2$ | √ | √ | NE | NE |
| RS-40-4 | (2-pyridyl-CH2) | $C_{28}H_{46}N_4O_2$ | √ | √ | NE | NE |

Synthesis of N-Sulfonamide-Pro-Pro-NH dodecylamides and PRCP inhibition data

Scheme 5

Table 5.

| R | Mol. Formula | Analyses H¹NMR   MS | rPRCP Ki (μM) | PRCP-dependent PK activation on HPAEC Ki (μM) |
|---|---|---|---|---|
| H₃C—(C₆H₄)— | C₂₉H₄₇N₃O₄S₁ | √ | NE | NE |
| (H₃C)₃C—CH₂—(C₆H₄)— | C₃₃H₅₅N₃O₄S₁ | √ | NE | NE |
| camphor-yl | C₃₂H₅₅N₃O₅S₁ | √ | NE | NE |
| H₃C— | C₂₃H₄₃N₃O₄S₁ | √ | NE | NE |

Synthesis of N-Urea-Pro-Pro-NH dodecylamides and PRCP inhibition data

Scheme 6

Table 6.

| R | Mol. Formula | Analyses | | rPRCP Ki (µM) | PRCP-dependent PK activation on HPAEC Ki (µM) |
|---|---|---|---|---|---|
| | | H¹NMR | MS | | |
| - | $C_{26}H_{43}N_5O_3$ | √ | √ | Not tested | Not tested |
| - | $C_{27}H_{46}IN_5O_3$ | | √ | Not tested | Not tested |
| (benzyl-NH) | $C_{30}H_{48}N_4O_3$ | √ | √ | NE | NE |
| (4-Cl-benzyl-NH) | $C_{30}H_{47}ClN_4O_3$ | | √ | NE | NE |
| (dichlorobenzyl-NH) | $C_{30}H_{46}Cl_2N_4O_3$ | | √ | NE | NE |

Synthesis of N-Carbamate-Pro-Pro-NH dodecylamides and PRCP inhibition data

Scheme 7

Table 7.

| Compound Number | Mol. Formula | Analyses H¹NMR   MS | rPRCP Ki (µM) | PRCP-dependent PK activation on HPAEC Ki (µM) |
|---|---|---|---|---|
| RS-45-30 | $C_{30}H_{47}N_3O_5$ | √ | NE | NE |

Synthesis of N-Amide-Pro-Pro-NH dodecylamides and PRCP inhibition data

Scheme 8

Table 8.

| Compound Number | R | Mol. Formula | Analyses H¹NMR   MS | rPRCP Ki (μM) | PRCP-dependent PK activation on HPAEC Ki (μM) |
|---|---|---|---|---|---|
| RS-61-5 | Cbz-HN-imidazole | $C_{36}H_{54}N_6O_5$ | √ | NE | NE |

Fig. 9A  Synthesis of proline A-ring isosteres and PRCP inhibition data
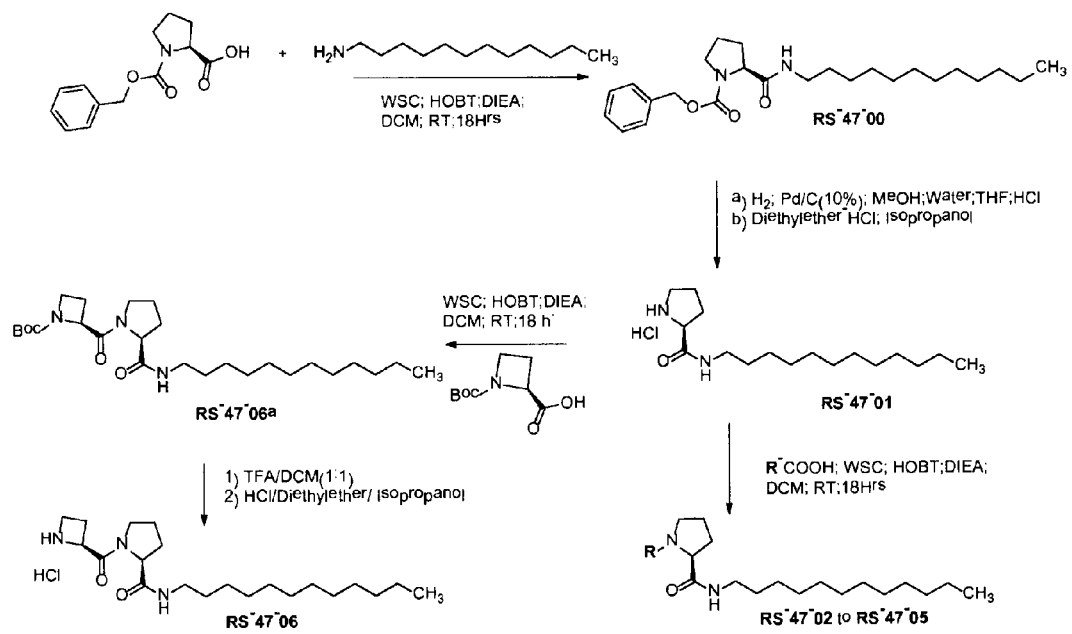

Fig. 9B

Scheme 9

Table 9.

| Compound Number | R | Mol. Formula | Analyses H$^1$NMR MS | | rPRCP Ki (µM) | PRCP-dependent PK activation on HPAEC Ki (µM) |
|---|---|---|---|---|---|---|
| RS-47-00 | - | C$_{25}$H$_{40}$N$_2$O$_3$ | √ | √ | NE | NE |
| RS-47-01 | - | C$_{17}$H$_{34}$N$_2$O | √ | √ | 61.5 | 477 |
| RS-47-02 | (pyrrole-2-carbonyl) | C$_{22}$H$_{37}$N$_3$O$_2$ | √ | √ | NE | NE |
| RS-47-03 | (thiazolidine-4-carbonyl) | C$_{21}$H$_{39}$N$_3$O$_2$S | √ | √ | NE | NE |
| RS-47-04 | (N-acetyl-cysteinyl) | C$_{22}$H$_{41}$N$_3$O$_3$S | √ | √ | NE | NE |
| RS-47-05 | (tetrahydroisoquinoline-3-carbonyl) | C$_{27}$H$_{43}$N$_3$O$_2$ | √ | √ | NE | NE |
| RS-47-06a | - | C$_{26}$H$_{47}$N$_3$O$_4$ | | √ | Not tested | Not tested |
| RS-47-06 | - | C$_{21}$H$_{39}$N$_3$O$_2$ | √ | √ | 43.7 | 17.4 |

Fig. 10A  Synthesis of proline B-ring isosteres and PRCP inhibition data
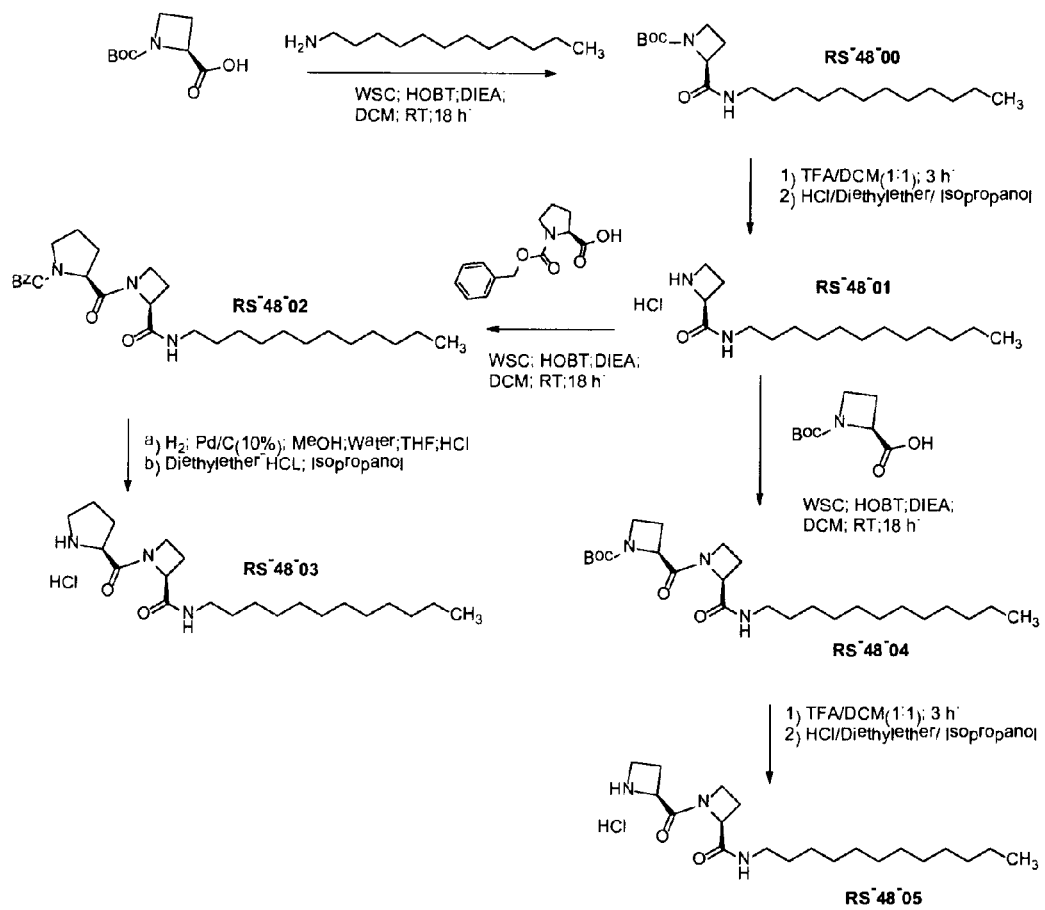

Fig. 10B

Scheme 10

Table 10.

| Compound Number | Mol. Formula | Analyses H¹NMR MS | | rPRCP Ki ($\mu M$) | PRCP-dependent PK activation on HPAEC Ki ($\mu M$) |
|---|---|---|---|---|---|
| RS-48-00 | $C_{21}H_{40}N_2O_3$ | | √ | Not Tested | Not Tested |
| RS-48-01 | $C_{16}H_{32}N_2O$ | √ | √ | 195.1 | 50.14 |
| RS-48-02 | $C_{29}H_{45}N_3O_4$ | √ | √ | Not Tested | Not Tested |
| RS-48-03 | $C_{21}H_{39}N_3O_2$ | √ | √ | 84.9 | 60.4 |
| RS-48-04 | $C_{25}H_{45}N_3O_4$ | | √ | Not Tested | Not Tested |
| RS-48-05 | $C_{20}H_{37}N_3O_2$ | √ | √ | 108.9 | 29.6 |

Synthesis of Z-Pro-GABA-NH-amides and PRCP inhibition data

Scheme 11

Table 11.

| R | Mol. Formula | Analyses H¹NMR  MS | rPRCP Ki (µM) | PRCP-dependent PK activation on HPAEC Ki (µM) |
|---|---|---|---|---|
| (2-Cl-benzyl) | $C_{24}H_{28}Cl_2N_3O_4$ | √   √ | 332.3 | 694.3 |
| (3-Cl-benzyl) | $C_{24}H_{28}Cl_1N_3O_4$ | √ | 227.7 | 565.7 |
| (4-Cl-benzyl) | $C_{24}H_{28}Cl_1N_3O_4$ | √ | 258.5 | 668.6 |
| (2,4-diCl-benzyl) | $C_{24}H_{27}Cl_2N_3O_4$ | √ | 147.7 | 604.3 |
| (3,4-diCl-benzyl) | $C_{24}H_{27}Cl_2N_3O_4$ | √ | 110.8 | 456.4 |
| (alkyl-CH₃) | $C_{29}H_{47}N_3O_4$ | √   √ | NE | 58 |
| (PEG-CH₃) | $C_{26}H_{41}N_3O_7$ | √   √ | 350.8 | 192.9 |

Synthesis of N-R-Pro-GABA-NH-dodecylamides and PRCP inhibition data

Scheme 12

Table 12

| R | Mol. Formula | Analyses H¹NMR MS | | rPRCP Ki (µM) | PRCP-dependent PK activation on HPAEC Ki (µM) |
|---|---|---|---|---|---|
| - | $C_{21}H_{41}N_3O_2$ | √ | √ | 36.9 | 6.4 |
| (benzyl) | $C_{28}H_{47}N_3O_2$ | | √ | NE | NE |
| (4-pyridyl) | $C_{27}H_{46}N_4O_2$ | √ | √ | NE | NE |
| (3-pyridyl) | $C_{27}H_{46}N_4O_2$ | √ | √ | NE | NE |
| (2-pyridyl) | $C_{27}H_{46}N_4O_2$ | √ | √ | NE | NE |
| (N-methylimidazolyl) | $C_{26}H_{47}N_5O_2$ | √ | √ | NE | NE |

Synthesis of N-Sulfonamide-Pro-GABA-NH-dodecylamides and PRCP inhibition data

Scheme 13

Table 13.

| Compound Number | R | Mol. Formula | Analyses H¹NMR MS | | rPRCP Ki (µM) | PRCP-dependent PK activation on HPAEC Ki (µM) |
|---|---|---|---|---|---|---|
| RS-44-01 | H₃C—⟨⟩— | $C_{28}H_{47}N_3O_4S_1$ | √ | √ | NE | NE |
| RS-44-02 | H₃C-C(CH₃)(CH₃)-⟨⟩— | $C_{32}H_{55}N_3O_4S_1$ | | √ | NE | NE |
| RS-44-03 | (camphor-like structure) | $C_{31}H_{55}N_3O_5S_1$ | | √ | NE | NE |
| RS-44-04 | H₃C— | $C_{22}H_{43}N_3O_4S_1$ | | √ | NE | NE |

Synthesis of N-Amide-Pro-GABA-NH-dodecylamides and PRCP inhibition data

Scheme 14

Table 14.

| Compound Number | R | Mol. Formula | Analyses H¹NMR MS | rPRCP Ki (µM) | PRCP-dependent PK activation on HPAEC KI (µM) |
|---|---|---|---|---|---|
| RS-61-2 | (N-methylimidazole carbonyl) | $C_{26}H_{45}N_5O_3$ | √ | NE | NE |
| RS-61-3 | (benzimidazole propanoyl) | $C_{31}H_{45}N_5O_3$ | √ √ | NE | NE |
| RS-61-4 | (Cbz-His) | $C_{35}H_{54}N_6O_5$ | √ | NE | NE |

Fig.15

Table 15

Effect of RS-33-21 on recombinant prolylcarboxypeptidase (rPRCP), serine proteases and carboxypeptidases

| Blocking agent | $K_i$ (μM) | | | | | | | | |
|---|---|---|---|---|---|---|---|---|---|
| | rPRCP | Kallikrein | FXIIa | FXIa | Trypsin | CPA | CPB | CPN | CPM |
| RS-33-21 | 43 | NE | NE | NE | NE | NE | NE | NE | NE |
| SBTI | NE | 6.15 | NT | 0.62 | 0.12 | NT | NT | NT | NT |
| CTI | NT | NT | 0.12 | NT | NT | NT | NT | NT | NT |
| 1,10- Phenanthroline | NE | NT | NT | NT | NT | 486 | 738.5 | 615.4 | 393.85 |

Inhibitor concentrations required to produce 50% inhibition of recombinant prolylcarboxypeptidase, various abundant serine proteases, and carboxypeptidases. rPRCP; recombinant prolylcarboxypeptidase, FXIIa; activated factor XII, FXIa; activated factor XI, CPA; carboxypeptidase A; CPB; carboxypeptidase B, CPN; carboxypeptidase N, CPM; carboxypeptidase M, SBTI; soy bean trypsin inhibitor, CTI; corn trypsin inhibitor.*NE : denotes no effect

**NT : indicates not tested

Fig 16

Table 16. Hepatic and renal toxicity of RS-33-21 in mice

| Metabolic panel | Vehicle | RS-33-21 (400 μM) |
|---|---|---|
| ALB | 3.9 | 3.9 |
| ALP | 80 | 93 |
| ALT | 34 | 33 |
| AMY | 822 | 1041 |
| TBIL | 0.4 | 0.4 |
| BUN | 16 | 19 |
| $Ca^{2+}$ | 9.9 | 9.9 |
| PHOS | 10 | 8.0 |
| CRE | 0.2 | 0.3 |
| GLU | 195 | 165 |
| Na+ | 152 | 151 |
| K+ | 5.8 | 5.4 |
| TP | 5.4 | 5.3 |
| GLOB | 1.5 | 1.5 |

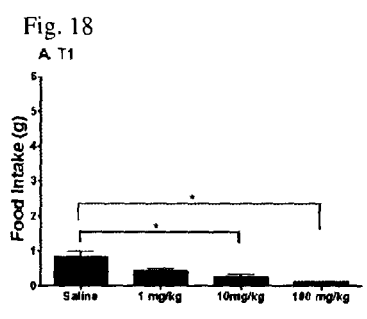
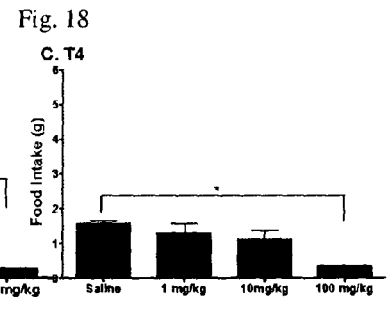
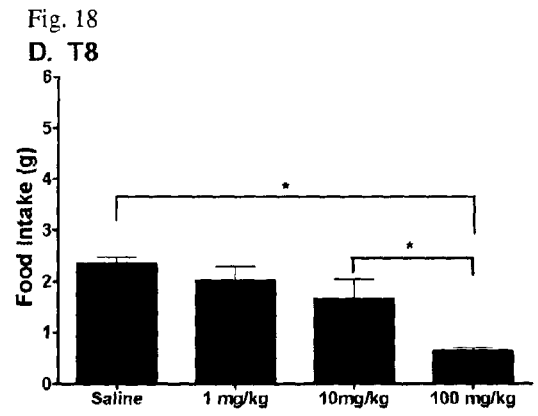
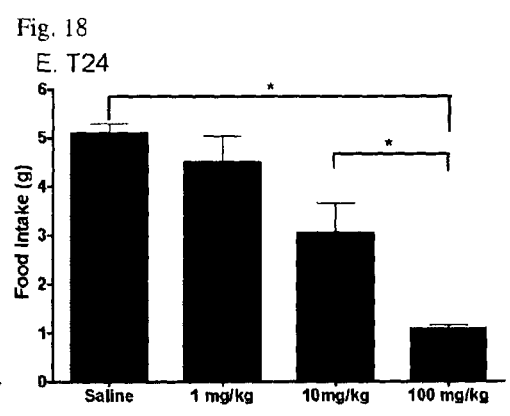
Fig. 18 A. T1
Fig. 18 B. T2
Fig. 18 C. T4
Fig. 18 D. T8
Fig. 18 E. T24

SELECTIVE INHIBITORS OF PROLYLCARBOXYPEPTIDASE

CROSS-REFERENCE TO RELATED APPLICATIONS

This is a §371 National Stage Application of International Application No. PCT/US2011/062889 filed 1 Dec. 2011 (1 Dec. 2010), pending, which claims priority of U.S. Provisional Application No. 61/418,708 filed 1 Dec. 2010 (1 Dec. 2010), the entire contents of which are incorporated herein by reference in their entirety.

SUPPORT FOR THE INVENTION

This invention was made with Government support under NCRR/NIH/P20RR021929 awarded by the National Institutes of Health. The United States Government has certain rights in this invention.

FIELD OF THE INVENTION

The present invention relates to the preparation of and the evaluation of serine protease prolylcarboxypeptidase (PRCP) inhibitors especially in their use in the field of weight management and in the preparation of medications for the treatment and management of obesity. Further, the present invention relates to new anorexigenic and anti-inflammatory drugs, acting through PRCP-mediated mechanisms.

BACKGROUND OF THE INVENTION

Obesity is a major risk factor for type 2 diabetes mellitus.[1,2] The proopiomelanocortin (POMC)-derived peptide, α-melanocyte-stimulating hormone (α-MSH) is involved in the regulation of food intake and energy homeostasis in mammals[3] and the reduction of inflammatory reactions.[4-6] Evidence indicates that the expression of α-MSH mRNA is increased in the pituitary of genetically obese mice (ob/ob)[7] and that α-MSH suppresses feeding behavior in mice and fish.[8,9] On the basis of evolutionary conservation theory, studies suggest that α-MSH has a species-dependent regulatory function in energy homeostasis and has two tissue-dependant and opposing roles. In the central nervous system (CNS), α-MSH increases sensitivity to insulin,[10] while in the periphery, α-MSH seems to play a pivotal role in insulin resistance.[10] α-MSH is a potent agonist of melanocortin 1 receptors (MC1R) and melanocortin 4 receptors (MC4R).[11] MC4R knockout mice have been shown to develop a maturity onset obesity syndrome characterized by hyperphagia, hyperglycemia and hyperinsulinemia.[12] It is shown that MC4R mutations are linked to severe obesity in French children with variable expression and penetrance.[13] Additionally, MTII (a specific synthetic MC3R/MC4R agonist) inhibits food intake in rats.[14] Notably, studies indicate that analogs of α-MSH influence blood glucose in mouse models of obesity.[10]

Recent studies have shown that the serine protease prolylcarboxypeptidase (PRCP) inactivates α-MSH by catalyzing the cleavage of the carboxyl terminus Pro-Val, suggesting that PRCP may have orexigenic action.[15] PRCP activates three distinct and seemingly unrelated (Ang II, Ang 1-8) to angiotensin 1-7 (Ang 1-7), and angiotensin III (Ang III, Ang 2-8) to angiotensin 2-7 (Ang 2-7); ii. PRCP potentiates vasodilation via activation of the plasma kallikrein-kinin system (KKS), resulting in the release of bradykinin (BK) from high molecular weight kininogen (HK).[16] BK is an important vascular mediator, causing vasodilation and is a leading inducer of edema;[17,18] iii. PRCP mediates cell growth and inflammation via inactivation of α-MSH.

Current medications for obesity are limited in effectiveness, suggesting the existence of a novel, uncharacterized mechanism that contributes to this condition. Since mutations in the MC4R gene can cause monogenic obesity,[19] applicants proposed that selective inhibitors of PRCP might be a promising therapeutic option for some people with elevated PRCP-induced α-$MSH_{1-12}$ production, especially those for whom other anti-obesity therapy has failed. The advantages of this approach are three-fold. First, PRCP inhibitors decrease inflammation through reducing the synthesis of BK and Ang 1-7. Secondly, PRCP inhibitors may promote the activation of anti-inflammatory mediators via MC1R-dependent and MC1R-independent pathways, acting through an α-MSH/NF-κB and/or α-MSH/IL10-mediated mechanisms.[6,20,21] Thirdly, PRCP inhibitors reduce food-intake in patients via MC4R, acting through an α-MSH-mediated mechanism. PRCP inhibitors may represent a new class of dual-acting anorexigenic and anti-inflammatory agents, which may reduce the risk of heart disease in obese patients. Recently, researchers have disclosed the identification of a potent and selective small molecule PRCP inhibitor to validate PRCP as a valid target for the development of anti-obesity drugs.[22]

SUMMARY OF THE INVENTION

Recent studies suggest that the PRCP plays a critical role in weight maintenance via the rapid inactivation of the anorexigenic peptide alpha-melanocyte-stimulating hormone (α-MSH). The present application describes on-going investigations that have demonstrated that over-activation of PRCP is linked to the inflammatory response, and PRCP inhibitors may reduce inflammation. Applicants have synthesized and evaluated a library of proline-based analogs as prospective recombinant PRCP (rPRCP) inhibitors and inhibitors of PRCP-dependent prekallikrein (PK) activation on human pulmonary artery endothelial cells (HPAEC). (S)—N-dodecyl-1-((S)-pyrrolidine-2-carbonyl) pyrrolidine-2-carboxamide (RS-33-21) was selected for further evaluation from the initial assessment of its PRCP inhibitory action (Ki=43.1 µM) coupled with its ability to block PRCP-dependent PK activation on HPAEC (Ki=34.1 µM). Furthermore, RS-33-21 demonstrated excellent selectivity against a panel of carboxypeptidases and serine proteases, and also blocked BK generation and BK-induced permeability by 100%, suggesting that RS-33-21 may be useful in preventing the local production of large amounts of BK. The anorexigenic effect of RS-33-21 was established by evaluating the PRCP-induced augmentation of feeding behavior in mice. RS-33-21 reduced food intake in a dose- and time-dependent manner. Collectively, these results suggest that RS-33-21 may represent a new anorexigenic and anti-inflammatory drug, acting through PRCP-mediated mechanisms.

The present invention relates to compounds of the formulae:

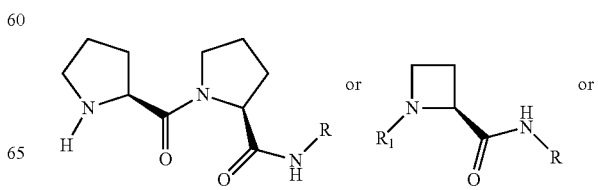

-continued

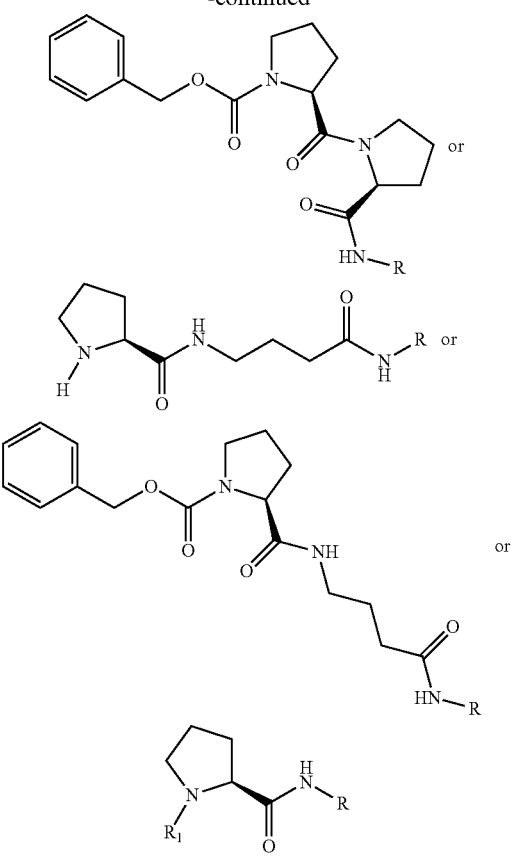

in which R is $C_5$-$C_{16}$ alkyl, $R_1$ is

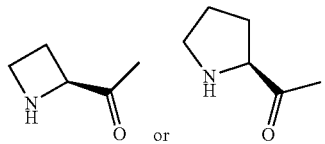

and isosteres and salts thereof.

The present invention further relates to pharmaceutical compositions comprising at least one compound of the formulae given above and a pharmaceutically acceptable carrier.

Additionally, this invention encompasses a method of treating a subject in need of anorexigenic and/or anti-inflammatory treatment comprising administering to the subject in need of the treatment an effective amount of at least one compound of the formulae shown above or a method which employs the pharmaceutical composition containing the compounds of the above formulae.

A still yet further aspect of the present invention are anorexigenic and/or anti-inflammatory compositions comprising at least one compound of the formulae shown above or pharmaceutical compositions containing the compounds of the above formulae.

Another aspect of the present invention relates to a method of treating obesity comprising administering to a subject in need of the treatment an effective amount of at least one compound of the formulae shown above or this same method in which a pharmaceutical composition containing at least one compound of the formulae given above is administered to a subject.

An embodiment of the present invention is the embodiment in which the alkyl group R of the formulae is $C_{12}H_{25}$.

Compounds of interest include:

RS-33-21

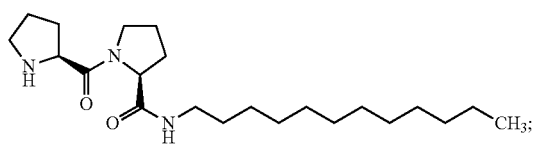

RS-48-03

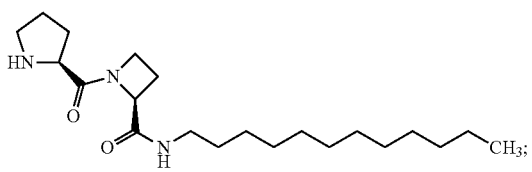

RS-48-05

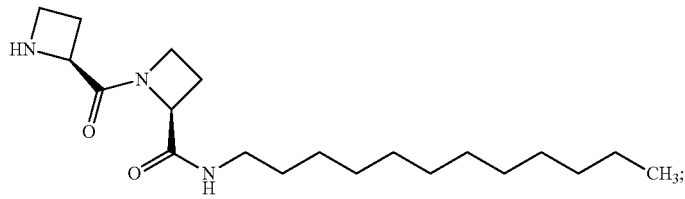

RS-42-01

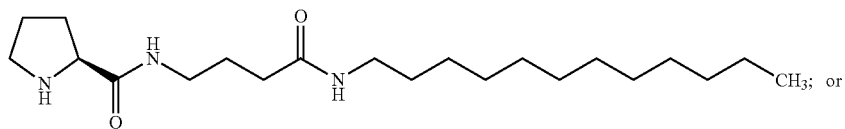

RS-47-06

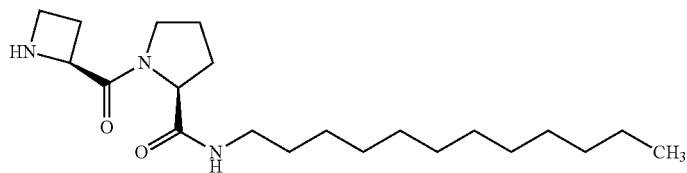

or isosteres or salts thereof.

BRIEF DESCRIPTION OF THE DRAWINGS

The accompanying drawings, which are incorporated in and form a part of the specification, illustrate the preferred embodiments of the present invention, and together with the description serve to explain the principles of the invention:

FIG. 1A (Scheme 1A and Table 1A)—Synthesis of Z-Pro-Pro-NH amides and PRCP inhibition data;

FIG. 1B (Scheme 1B and Table 1B)—Synthesis of Z-Pro-Pro-NH amides and PRCP inhibition data;

FIG. 3 (Scheme 3 and Table 3)—Synthesis of N—R-Pro-Pro-NH dodecylamides and PRCP inhibition data;

FIG. 9A—Synthesis of proline A-ring isosteres and PRCP inhibition data;

FIG. 9B (Scheme 9 and Table 9)—Synthesis of proline A-ring isosteres and PRCP inhibition data;

FIG. 10A—Synthesis of proline B-ring isosteres and PRCP inhibition 5 data;

FIG. 10B (Scheme 10 and Table 10)—Synthesis of proline B-ring isosteres and PRCP inhibition 5 data;

FIG. 15—Table 15—Effect of RS-33-21 on recombinant prolylcarboxypeptidase (rPRCP), serine proteases and carboxypeptidases;

FIG. 16A Effects of RS-33-21 on recombinant PRCP;

FIG. 16B Effects of RS-33-21 on PRCP-dependent prekallikrein activation in human pulmonary vein artery endothelial cells (HPAEC);

FIG. 16C RS-33-21 inhibits the metabolism of $BK_{1-8}$ to $BK_{1-7}$ by rPRCP;

FIG. 16D RS-33-21 blocks the metabolism of Ang III (angiotensin 2-8) to $Ang_{2-7}$ by rPRCP;

FIG. 16E RS-33-21 is a competitive inhibitor of PRCP;

FIG. 18 Effect of RS-33-21 on food intake of mice.

DETAILED DESCRIPTION OF THE INVENTION

Figure 2:
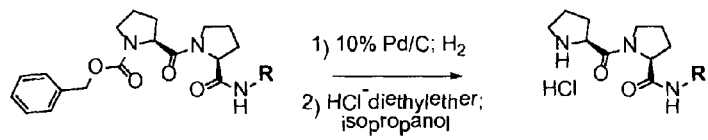
FIG. 2 (Scheme 2 and Table 2)—Synthesis of NH-Pro-Pro-NH amides and PRCP inhibition data.

As used herein, the term "comprising" means various components can be conjointly employed in the pharmaceutical composition of this invention. Accordingly, the terms "consisting essentially of" and "consisting of" are embodied in the term comprising.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will, obviously, vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutical addition salts" includes a pharmaceutically acceptable salt of the anti-cancer compound. These include acid salts of the amines.

As used herein, a "pharmaceutical carrier" is a pharmaceutically acceptable solvent, suspending agent or vehicle for delivering the anti-obesity agents of this invention to the animal or human. The carrier may be liquid or solid and is selected with the planned manner of administration in mind.

As used herein useful acids for salt formation include, for example, acetic acid, adipic acid, L-ascorbic acid, L-, capric, carbonic, citric, fumaric, galactaric, D-glucoheptanoic, D-gluconic, D-glucuronic, glutamic, glutaric, glycerophosphoric, hippuric, hydrochloric, DL-lactic, lauric, maleic, (−)-L-malic, phosphoric, sebacic, succinic, sulphuric, (+)L-tartaric, and thiocyanic. Glycolic aspartic, palmitic, stearic alginic, benzenesulfonic, benzoic, (+)camphoric, caprylic, cyclamic, dodecylsulfuric, ethane-1,2-disulfonic, methanesulfonic, ethanesulfonic, 2-hydroxy-, gentisic, 2-oxo glutaric, isobutyric, lactobionic, malonic, methanesulfonic, naphthalene-1,5-disulfonic, naphthalene-2-sulfonic, 2-napthoic 1-hydroxy, nicotinic, oleic, orotic, oxalic, pamoic, propionic, (−)-L-pyroglutamic and p-toluenesulfonic acids.

The invention is further illustrated by the following non-limited examples. All scientific and technical terms have the meanings as understood by one with ordinary skill in the art. The specific examples which follow illustrate the synthesis of representative compounds of the instant invention and are not to be construed as limiting the invention in sphere or scope. The methods may be adapted to variation in order to produce compounds embraced by this invention but not specifically disclosed. Further, variations of the methods to produce the same compounds in somewhat different fashion will be evident to one skilled in the art. The synthetic descriptions and specific examples that follow are only intended for the purposes of illustration, and are not to be construed as limiting in any manner to make compounds of the present invention by other methods.

Figure 4:
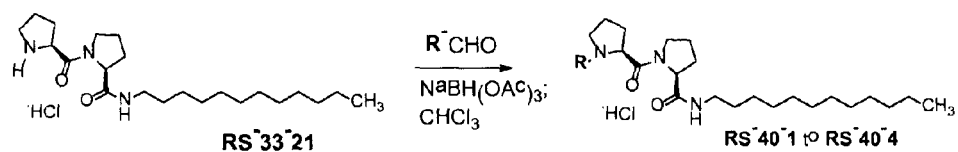
FIG. 4 (Scheme 4 and Table 4)—Synthesis of N—R-Pro-Pro-NH dodecylamides and PRCP inhibition data.
Figure 5:
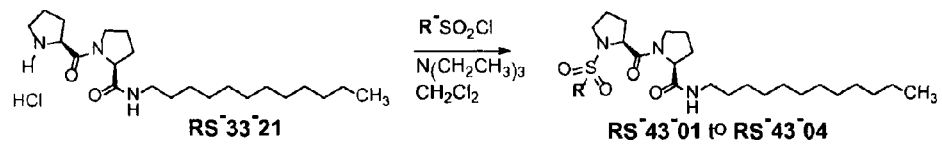
FIG. 5 (Scheme 5 and Table 5)—Synthesis of N-Sulfonamide-Pro-Pro-NH dodecylamides and PRCP inhibition data.
Figure 6:
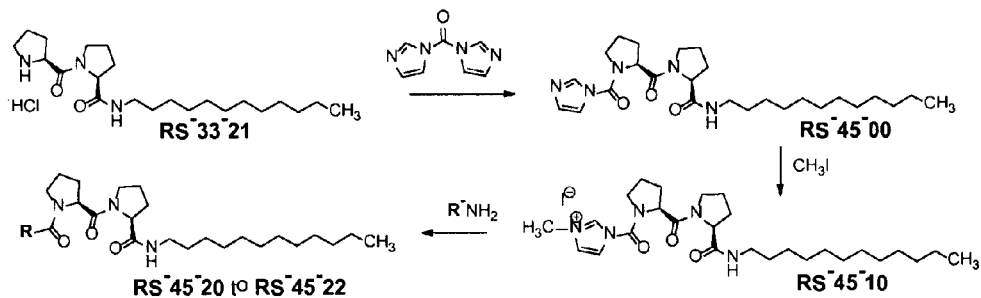
FIG. 6 (Scheme 6 and Table 6)—Synthesis of N-Urea-Pro-Pro-NH dodecylamides and PRCP inhibition data.
Figure 7:
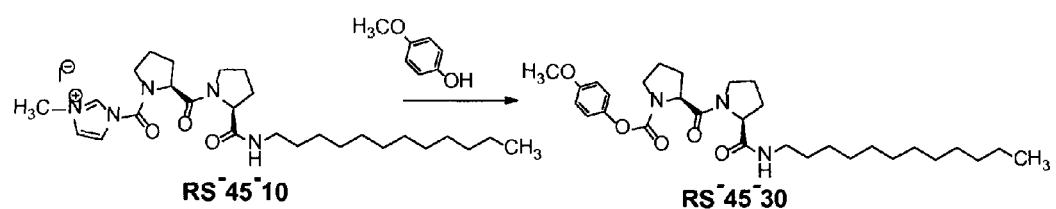
FIG. 7 (Scheme 7 and Table 7)—Synthesis of N-Carbamate-Pro-Pro-NH dodecylamides and PRCP inhibition data.
Figure 8:
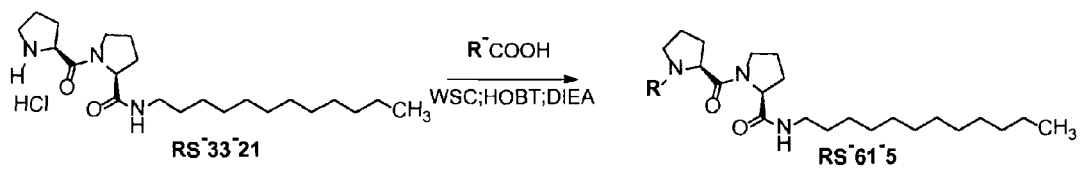
FIG. 8 (Scheme 8 and Table 8)—Synthesis of N-Amide-Pro-Pro-NH dodecylamides and PRCP inhibition data.

Several laboratories including applicants have shown that 1-[1-(benzyloxycarbonyl)-L-prolyl]prolinal (Z-Pro-Pro-OH) inhibits PRCP with an $IC_{50}>1$ mM. Using Z-Pro-Pro-OH as a lead, applicants initially synthesized a number of proline B-ring amide analogs (Z-Pro-Pro-NH amides) by condensing Z-Pro-Pro-OH with various primary amines under standard conditions to yield analogs RS-33-1 to RS-33-29 (FIG. 1A, Scheme 1A and FIG. 1B, Scheme 1B). PRCP assay-guided evaluation resulted in the selection of RS-33-20 (containing the dodecyl group) for further optimization. The N-benzyloxycarbonyl group of lead inhibitor RS-33-20 was removed under standard catalytic hydrogenation conditions ($H_2$, Pd/C) and the amine product RS-33-21 was converted to its corresponding HCl salt. Other select N-benzyloxycarbonyl derivatives were also subjected to the catalytic hydrogenation reaction and converted to their corresponding hydrochloride salts (FIG. 2, Scheme 2). RS-33-21 was reacted with (3-bromopropyl)benzene in diisopropylethylamine to yield RS-33-201 (FIG. 3, Scheme 3) or with various aldehydes under reductive amination reaction conditions (RCHO, NaBH(OAc)$_3$) affording analogs RS-40-1 to RS-40-4 (FIG. 4, Scheme 4). Proline A-ring sulfonamide derivatives (RS-43-01 to RS-43-04) were prepared from RS-33-21 by reaction with their respective sulfonyl chlorides (FIG. 5, Scheme 5). Proline A-ring urea derivatives (RS-45-20 to RS-45-22) were synthesized from intermediate RS-45-10 by reaction with benzylamine reagents (FIG. 6, Scheme 6). A proline A-ring carbamate (RS-45-30) was prepared from reaction of intermediate RS-45-10 with 4-methoxyphenol (FIG. 7, Scheme 7). Condensation of RS-33-21 with a suitably protected amino acid under the standard condensation reaction yielded RS-61-5 (FIG. 8, Scheme 8). FIG. 9B, Scheme 9 depicts the reaction sequence used for the synthesis of proline A-ring bioisosteres. Reaction of Z-Pro-OH with dodecylamine under standard condensation reactions yielded RS-47-00, which was deprotected using catalytic hydrogenation to afford amine RS-47-01. RS-47-01 was condensed with various carboxylic acids to yield analogs RS-47-02 to RS-47-05, or condensed with (S)-1-(tert-butoxycarbonyl)azetidine-2-carboxylic acid to afford RS-47-06a, which was subsequently 5 subjected to treatment with trifluoroacetic acid in dichlormethane yielding RS-47-06. FIG. 10B, Scheme 10 depicts the synthesis of azetidine bioisosteres, serving as a surrogate to the proline B-ring. (S)-1-(tert-butoxycarbonyl)azetidine-2-carboxylic acid was reacted with dodecylamine under the standard condensation reaction to afford RS-48-00, which was treated with trifluoroacetic acid in dichloromethane to yield RS-48-01. RS-48-01 was reacted with either (S)-1-(tert-butoxycarbonyl)azetidine-2-carboxylic acid or (S)-1-(benzyloxycarbonyl)pyrrolidine-2-carboxylic acid under standard condensation reaction conditions to yield RS-48-04 and RS-48-02 respectively. Standard methods of deprotection yielded RS-48-05 and RS-48-03, characterized and tested as their respective hydrochloride salts.

Figure 11:
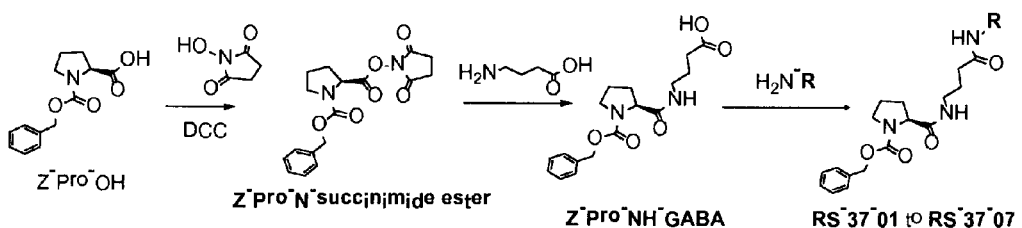
FIG. 11 (Scheme 11 and Table 11)—Synthesis of Z-Pro-GABA-NH-amides and PRCP inhibition data.
Figure 12:
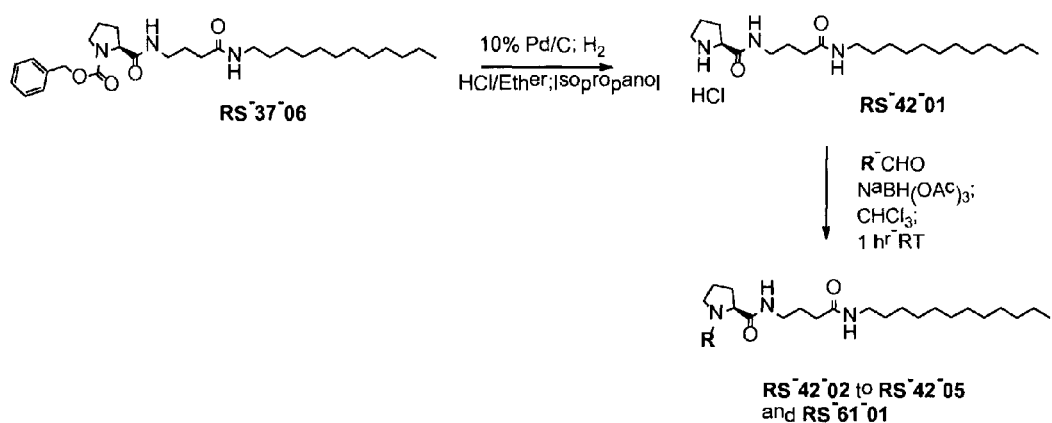
FIG. 12 (Scheme 12 and Table 12)—Synthesis of N—R-Pro-GABA-NH-dodecylamides and PRCP inhibition data.
Figure 13:
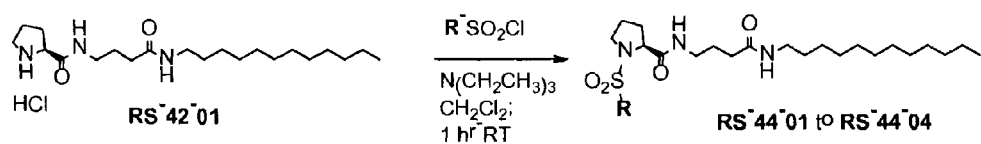
FIG. 13 (Scheme 13 and Table 13)—Synthesis of N-Sulfonamide-Pro-GABA-NH-dodecylamides and PRCP inhibition data.
Figure 14:
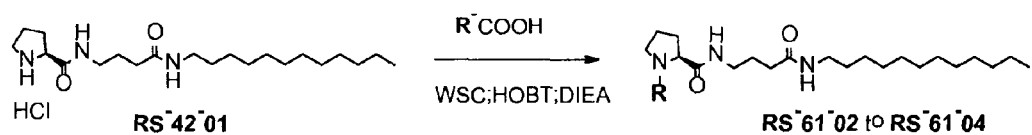
FIG. 14 (Scheme 14 and Table 14)—Synthesis of N-Amide-Pro-GABA-NH-dodecylamides and PRCP inhibition data.

FIG. 11, Scheme 11 depicts the synthesis of proline B-ring acyclic bioisosteres. Reaction of an activated ester (N-hydroxysuccinimide ester of Z-Pro-OH) with 4-aminobutanoic acid yielded the Z-Pro-GABA intermediate, that was condensed with a series of amines to yield analogs RS-37-01 to RS-37-07. The Z-Pro-GABA analog with a dodecylamine substituent (RS-37-06) was subjected to catalytic hydrogenation yielding RS-42-01 (converted to its corresponding hydrochloride salt). RS-42-01 was reacted with aldehydes under standard reductive amination reaction conditions yielding compounds RS-42-02 to RS-42-05 and RS-61-01 (FIG. 12, Scheme 12). RS-42-01 was reacted with either sulfonyl chlorides or carboxylic acids to yield sulfonamides (RS-44-01 to RS-44-04; FIG. 13, Scheme 13) and amide analogs (RS-61-02 to RS-61-04; FIG. 14, Scheme 14) respectively.

Applicants utilized two assays to evaluate the putative PRCP inhibitors; 1.) a chromogenic enzyme assay, that involved the continual monitoring [60 min] for the production of p-nitroaniline derived from rPRCP-catalyzed conversion of Ala-Pro-p-nitroaniline (APpNA) in the presence of inhibitor and; 2.) a cell-based assay measuring the PRCP-dependent PK activation on human pulmonary artery endothelial cells (HPAEC). An initial set of simple Z-Pro-Pro-NH-amide derivatives were evaluated, and it was determined that the most dramatic PRCP inhibitory effects were observed in the homologous NH-alkyl series of compounds with RS-33-20 inhibiting both rPRCP ($K_i$=61.5 μM) and the activation of PK to kallikrein by PRCP on HPAEC ($K_i$=64.3 μM). The length of the carbon group was optimal for C12 substitution (dodecyl), but the requirement for a saturated hydrocarbon was not apparent. To test this hypothesis, applicants substituted an ethoxy-3-propyl repeating unit (RS-33-22) for the dodecane group in RS-33-20. Analog RS-33-22 was ineffective in inhibiting rPRCP or blocking PK activation suggesting a key role for the hydrocarbon dodecane moiety. Aqueous solubility was limited for a number of analogs, particularly those with logP values greater than 3.5. Since the rPRCP inhibitory effects of compound RS-33-20 were modest, further structural optimization commenced with replacing the N-CBz group with a series of heterocyclic groups to generate proline A-ring N-benzyl amines, suitable precursors for making HCl salts. None of these derivatives inhibited PRCP in either the enzyme or cell-based assay (Scheme 4, Table 4). However, the compound lacking a proline A-ring substituent (RS-33-21) proved to be an effective inhibitor of PRCP ($K_i$=43.1 μM) and furthermore blocked PRCP-dependent PK activation on HPAEC's ($K_i$=34.1 μM) Further insight was realized with the replacement of proline ring-B with a flexible GABA spacer group (Scheme 11, Table 11). The dodecyl analog RS-37-06 was most effective in its ability to block the conversion of PK to kallikrein on HPAEC with an $K_i$ of 37 μM (Scheme 11, Table 11), but failed to block rPRCP in the enzyme assay (due largely to limited solubility in PRCP assay media). Further modification of the Z-Pro-GABA-NH amide series optimized with the docecyl amide group resulted in similar SAR profiles, with the compound lacking the proline A-ring N-substituent (RS-42-01) demonstrating potent rPRCP inhibition ($K_i$=37 μM) and PK activation blockade ($K_i$=6.4 μM) (Scheme 12, Table 12).

Replacement of the proline ring-A with a number of heterocyclic isosteres afforded analogs RS-47-02 to RS-47-05, among which, only the azetidine analog RS-47-06 exhibiting potent rPRCP inhibition (See Scheme 9, Table 9). The construction of proline-B ring azetidine isosteres (compounds RS-48-01, RS-48-03, RS-48-05) further established the requirement for an unsubstituted N-group (See Scheme 10, Table 10).

RS-33-21 is a Selective PRCP Inhibitor

Applicants chose RS-33-21 from the library of analogs based on the initial enzyme- and cell-based assay inhibition results against rPRCP, and further evaluated the effect of RS-33-21 on the most abundant plasma serine proteases. Compounds RS-33-21 and RS-42-01 inhibited rPRCP in a dose-dependent manner with an $K_i$ value of 43.1 µM (FIG. 16A). These compounds also blocked PK activation induced by PRCP on HPAEC (FIG. 16B). Since blocking activity of RS-42-01 was not better than compound RS-33-21, applicants initially characterized and investigated the mechanism of action of RS-33-21 in vitro and in vivo. Further, kinetic studies showed that RS-33-21 is a competitive inhibitor of rPRCP at a concentration ranging from 3-100 µM (FIG. 16C).

RS-33-21 failed to inhibit kallikrein, FXIIa, FXIa, or trypsin at concentrations >1.0 mM. Furthermore, soybean trypsin inhibitor (SBTI) inhibited kallikrein, FXIa, and trypsin with $IC_{50}$ values of 10, 1.0, and 0.2 µM, respectively (FIG. 15, Table 15), while corn trypsin inhibitor blocked FXIIa with an $IC_{50}$ of 0.2 µM. Unlike PRCP, the carboxypeptidases CPN[23] and CPM[24] regulate kinins and are mainly involved in the chronic phase of the inflammatory response. While BK exerts its vasodilatory effect through the bradykinin B2 receptors (BKB2R), des-Arg9-BK (a substrate of PRCP) mediates its effect via the selective bradykinin B1 receptors (BKB1R). Given the weak internalization of BKB1R and its over expression during inflammation,[25] applicants hypothesized that the two serine carboxypeptidases (CPM and CPN) upstream of PRCP might have affinity for RS-33-21 during the chronic phase of inflammation. Applicants determined the effect of RS-33-21 on CPN (hCPN, partially purified from plasma[31]) and CPM. RS-33-21 did not inhibit the metabolism of hippuryl-lysine,[26, 27] while 1,10-phenanthroline blocked both CPN and CPM with $IC_{50}$ values of 1.0 and 0.64 mM respectively (FIG. 15, Table 15). Carboxypeptidase A (CPA) is a highly conserved protease, which is present in pancreas and the secretory granules of mast cells. Although its substrate selectivity is different than that of PRCP, both CPA and PRCP can cleave the C-terminal aromatic or aliphatic amino acids of proteins or peptides. The effect of RS-33-21 on carboxypeptidase A [CPA, EC 3.4.17.1] and carboxypeptidase B [CPB, EC 3.4.17.2] was determined. CPA and CPB were not inhibited by RS-33-21. However, 1,10-phenanthroline inhibited CPA and CPB with $IC_{50}$ values of 0.79 and 1.2 mM, respectively (FIG. 15, Table 15). The data demonstrate that RS-33-21 is a selective inhibitor of PRCP.

Effects of RS-33-21 on Angiotensin II and Bradykinin Metabolism.

Figure 17:
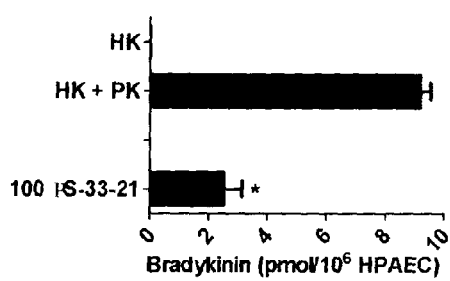
FIG. 17A RS-33-21 blocks bradykinin generation on HPAEC.
FIG. 17B RS-33-21 blocks bradykinin-induced nitric oxide generation on HPAEC.
FIG. 17C RS-33-21 blocks bradykinin-induced prostacyclin generation on HPAEC.
FIG. 17D RS-33-21 blocks bradykinin-induced HPAEC permeability.
Figure 17:
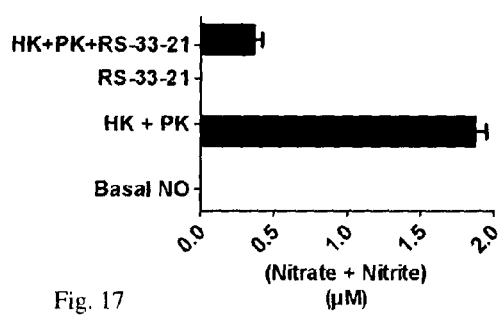
Figure 17:
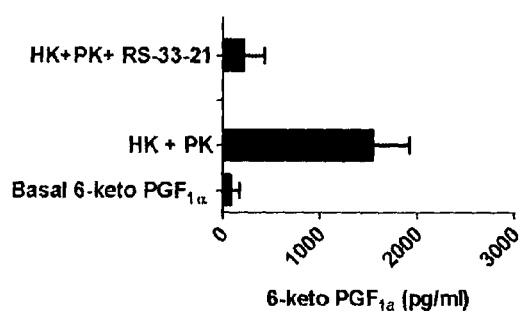
Figure 17:
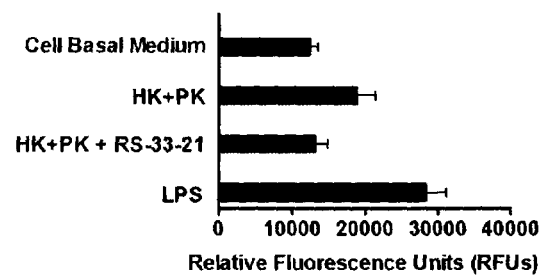

Applicants previously reported a LC/MS-based method that allowed for the characterization of angiotensin metabolism by rPRCP.[20] Applicants used this LC/MS method for evaluating the PRCP-catalyzed cleavage of Ang II to Ang 1-7 and BK 1-8 to BK 1-7 in the presence or absence of RS-33-21. RS-33-21 blocked the conversion of Ang II to Ang 1-7 (data not shown) in addition to the conversion of BK 1-8 to BK 1-7 by rPRCP (FIG. 17A). These results provide further evidence that RS-33-21 is a specific inhibitor of PRCP.

The Effect of RS-33-21 on the PRCP-Induced Production of Nitric Oxide (NO) and Prostacyclin ($PGI_2$).

PRCP-dependent PK activation results in generation of NO and $PGI_2$ in endothelial cells. Applicants determined the influences of RS-33-21 on formation of NO and $PGI_2$ after the assembly and activation of the complex of HK/PK. RS-33-21 (100 µM) prevented the production of both NO and $PGI_2$ by 80% (FIG. 17B, 17C).

Determination of the Effect of RS-33-21 on Cell Permeability.

Since RS-33-21 significantly blocked PK activation on endothelial cells, additional experiments were performed to determine its effects on the generation of bradykinin (BK) and cell permeability. The treatment of human pulmonary artery endothelial cell monolayer (HPAEC) with 0.1 µM of HK did not alter the endothelial permeability, whereas addition of the complex of HK/PK (0.1 µM each) resulted in a significant increase in endothelial permeability (FIG. 17D). These data suggest that the activation of PK can influence endothelial permeability, confirming a previously described report.[28] RS-33-21 (100 µM) reduced cell permeability by 90% (FIG. 17D)

Determination of the Toxicity of RS-33-21.

Figure 16:
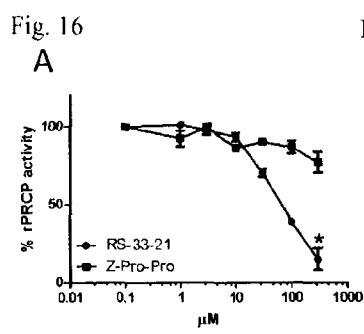
FIG. 16—Table 16—Hepatic and renal toxicity of RS-33-21 in mice.
Figure 16:
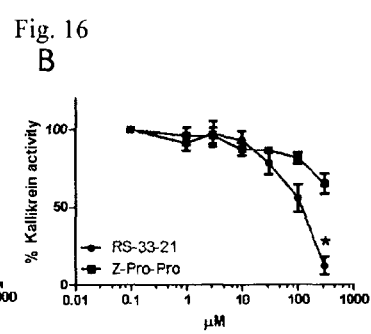
Figure 16:
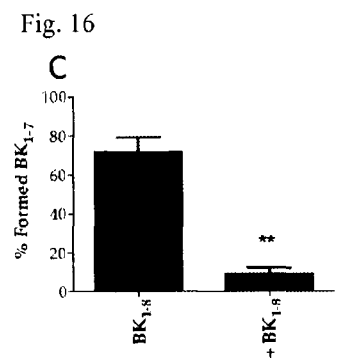
Figure 16:
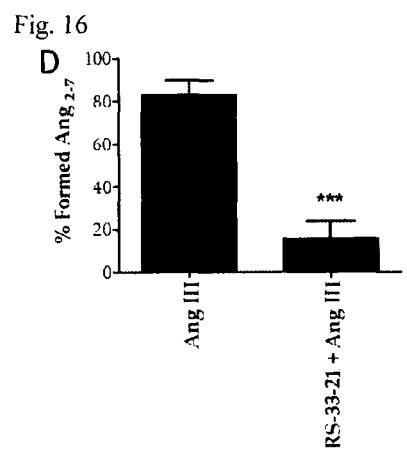
Figure 16:
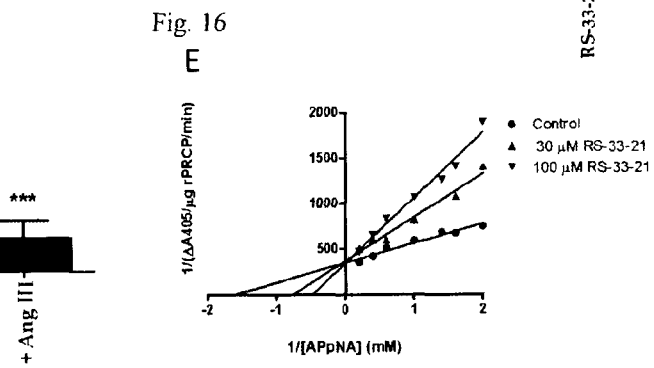

The effect of RS-33-21 on 14 metabolic markers was determined in mice (FIG. 16. Table 16) and it was shown that RS-33-21 failed to cause any significant change in electrolyte levels, body water, or the markers of kidneys and liver within 8 h. However, RS-33-21 caused a slight increase (20%) in blood amylase compared to the sham animals (n=3). The blood glucose level was decreased in drug-treated mice (n=3) by 15%.

Investigation of RS-33-21 on Food-Intake.

Applicants investigated the effect of intaperitoneal (i.p.) administration of RS-33-21 on food intake in mice. Injection of mice (randomized based on body weight) with RS-33-21 (i.p.; 1, 10, or 100 mg/kg) significantly ($p \le 0.05$) inhibited food intake (n=6) in a dose-dependent manner (FIG. 18). A single i.p. injection of RS-33-21 (100 mg/kg) significantly ($p \le 0.05$) reduced food intake in mice (n=6) for 24 h (FIG. 18).

Discussion

The goal of applicants' research and invention was to synthesize and evaluate compounds with inhibitory activity against human PRCP for evaluation as antiobesity agents. Applicants' data indicate that RS-33-21 is a selective inhibitor of PRCP and PRCP-dependent pathways. In addition, RS-33-21 reduced food-intake in mice in a dose- and time-dependent fashion. There is strong evidence suggesting that PRCP is involved both in inflammation and obesity.[13] PRCP is a proteolytic enzyme that promotes inflammation by generating kallikrein, BK, and Ang 1-7 at the site of injury.[29] Notably, there is evidence that the plasma kallikrein kinin system may be involved in obesity and the ethiopathogenesis of the metabolic syndrome.[34]

The role of the melanocortin system in food intake is established, and prevention of the rapid inactivation of α-MSH by PRCP may prove to be a better alternative pathway to potential obesity treatments. While α-MSH has both anti-inflammatory[30] and anorexigenic properties, PRCP has proinflammatory and orexigenic actions.[3] In theory, PRCP inhibitors are anorexigenic and anti-inflammatory agents.[3] Considering the central role of PRCP in obesity and inflammation, applicants synthesized and characterized the hypophagic effects of PRCP inhibitor. Applicants' data demonstrated that RS-33-21 inhibited PRCP-induced NO formation. The administration of RS-33-21 reduced food intake in mice in a dose-dependent and time-dependent manner. These findings suggest that RS-33-21 may represent a new anorectic drug and an anti-inflammatory agent.

Administration of the present anorectic drugs and an anti-inflammatory agents may be by any of the conventional routes of administration, for example, oral, subcutaneous, intraperitoneal, intramuscular, intravenous or rectally. In an embodiment of the invention, the compound can be administered in combination with a pharmaceutically acceptable carrier which may be solid or liquid, dependent upon choice and route of administration. Examples of acceptable carriers include, but are not limited to, starch, dextrose, sucrose, lactose, gelatin, agar, stearic acid, magnesium stearate, acacia, and similar carriers. Examples of liquids include saline, water, edible oils, e.g. peanut and corn oils.

When administered in solid form, the compound and diluent carrier may be in the form of tablets, capsules, powders, lozenges, suppositories prepared by any of the well known methods. When given as a liquid preparation, the mixture of active compound and liquid diluent carrier may be in the form of a suspension administered as such. The instant compounds can be administered in a non-toxic dosage concentration sufficient to produce an anorexigenic and anti-inflammatory effect. The actual dosage unit can be determined by the well recognized factors such as the body weight of a patient and/or the severity and type of pathological condition the patient might be suffering with. With these considerations in mind, the dosage unit for a particular patient can be readily determined by the medical practitioner in accordance with the techniques known in the medical arts.

EXPERIMENTAL SECTION

General Procedure for Synthesis of Z-Pro-Pro-NH-Amide Derivatives (FIG. 1A, Scheme 1A and FIG. 1B, Scheme 1B: RS-33-1 to RS-33-29).

1-(3-dimethylaminopropyl)-3-ethylcarbodiimide hydrochloride (WSC; 435 mg; 2.26 mmol; 1.3 eq), 1-hydroxybenzotriazole hydrate (HOBT; 353 mg; 2.61 15 mmol; 1.5 eq), N,N-diisopropylethylamine (Hunigs base; 249 mg; 357 µL) and a primary amine (1.92 mmol; 1.1 eq) were added to a stirring solution of Z-Pro-Pro-OH (600 mg; 1.74 mmol; 1 eq) in $CH_2Cl_2$ (20 mL). The reaction mixture was stirred at 25° C. for 18 h, then diluted with $CH_2Cl_2$ (20 mL), washed with 1M hydrochloric acid (1×20 mL), water (2×20 mL) and the combined aqueous washings were extracted with $CH_2Cl_2$ (2×20 mL). Combined organic fractions were dried over anhydrous $Na_2SO_4$, filtered, and the filtrate was evaporated under reduced pressure. The crude residue was purified by silica gel column chromatography using a mobile phase consisting of 5% methanol-95% ethyl acetate to afford the final coupled products (RS-33-1 to RS-33-29) in yields ranging from 31-92%. The $_1$HMR spectra reveal mixtures of amide/carbamate cis/trans rotamers (4 distinct rotational isomers) in approximately 2:1 to 4:1 ratios for the Z-Pro-Pro-amides and related analogs, as measured by the differences in the chemical shifts in $CDCl_3$ observed for the amide-NH proton of each conformer for benzylic amine substituents: [$\Delta S \propto \sim 0.7$ ppm ($\delta \sim 7.6$ and 8.2 ppm)] and for aliphatic amine substitutents [$\Delta \delta \sim 0.7$ ppm ($\delta \sim 7.7$ and 7.0 ppm). When discernable, the chemical shifts of the major rotamer are listed.

RS-33-1:
(S)-benzyl 2-((S)-2-(benzylcarbamoyl)pyrrolidine-1-carbonyl)pyrrolidine-1-carboxylate. From benzylamine. (87%); $^1$H NMR (400 MHz, $CDCl_3$) δ 7.55 (bd, J=6.3 Hz, 1H), 7.31 (m, 4H), 7.28-7.14 (m, 6H), 5.21-5.07 (m, 1H), 5.07-4.88 (m, 1H), 4.71-4.48 (m, 1H), 4.48-4.14 (m, 3H), 3.71 (dd, J=16.5, 8.6 Hz, 1H), 3.66-3.43 (m, 3H), 3.43-3.22 (m, 1H), 2.62-1.96 (m, 4H), 1.96-1.33 (m, 4H). MS (ESI+) m/z 458.1; calcd for $C_{25}H_{29}N_3O_4Na$ (MNa$^+$): 458.21.

RS-33-2:
(S)-benzyl 2-((S)-2-((3,4-dichlorobenzyl)carbamoyl)pyrrolidine-1-carbonyl) pyrrolidine-1-carboxylate. From 3,4-dichlorobenzylamine. (69%); $^1$H NMR (400 MHz, $CDCl_3$) δ 7.87 (t, J=5.9 Hz, 1H), 7.53-7.18 (m, 7H), 7.18-6.82 (m, 1H), 5.20-5.06 (m, 1H), 5.06-4.91 (m, 1H), 4.67-4.48 (m, 1H), 4.48-4.28 (m, 2H), 4.28-4.13 (m, 1H), 3.78-3.23 (m, 4H), 2.58-2.05 (m, 3H), 2.05-1.41 (m, 5H). MS (ESI+) m/z 526.08, 528.08; calcd for $C_{25}H_{27}Cl_2N_3O_4Na$ (MNa$^+$): 526.13, 528.13.

RS-33-3:
(S)-benzyl 2-((S)-2-((4-chlorophenethyl)carbamoyl)pyrrolidine-1-carbonyl)pyrrolidine-1-carboxylate. From 4-chlorophenethylamine. (75%); $^1$H NMR (500 MHz, $CDCl_3$) δ 7.86 (bs, 1H), 7.39-7.03 (m, 9H), 5.25-4.91 (m, 2H), 4.63-4.27 (m, 1H), 4.27-3.90 (m, 1H), 3.77-3.19 (m, 6H), 2.94-2.66 (m, 2H), 2.56-1.94 (m, 4H), 1.94-1.21 (m, 4H). MS (ESI+) m/z 506.0; calcd for $C_{26}H_{30}ClN_3O_4Na$ (MNa$^+$): 506.18.

RS-33-4:
(S)-benzyl 2-((S)-2-((2-methoxyphenethyl)carbamoyl)pyrrolidine-1-carbonyl) pyrrolidine-1-carboxylate. From 2-methoxyphenethylamine. (84%); $^1$H NMR (500 MHz, $CDCl_3$) δ 7.36-7.29 (m, 5H), 7.20-7.09 (m, 2H), 6.94 (bs, 1H), 6.88-6.80 (m, 2H), 5.41-4.85 (m, 2H), 4.67-3.93 (m, 2H), 3.81 (s, 3H), 3.74-3.22 (m, 6H), 3.11-2.70 (m, 2H), 2.53-1.22 (m, 8H). MS (ESI+) m/z 502.1; calcd for $C_{27}H_{33}N_3O_5Na$ (MNa$^+$): 502.23.

RS-33-5:
(S)-benzyl 2-((S)-2-(decylcarbamoyl)pyrrolidine-1-carbonyl)pyrrolidine-1-carboxylate. From n-decylamine. (66%); $^1$H NMR (400 MHz, $CDCl_3$) δ 7.70 (s, 1H), 7.29 (m, 5H), 5.29-4.89 (m, 2H), 4.68-4.15 (m, 2H), 3.82-3.03 (m, 6H), 2.61-1.63 (m, 8H), 1.60-1.14 (m, 16H), 0.87 (dd, J=7.9, 4.5 Hz, 3H). MS (ESI+) m/z 508.2; calcd for $C_{28}H_{43}N_3O_4Na$ (MNa$^+$): 508.31.

RS-33-6:
(S)-benzyl 2-((S)-2-(hexadecylcarbamoyl)pyrrolidine-1-carbonyl) pyrrolidine-1-carboxylate. From hexadecylamine (68%) $^1$H NMR (400 MHz, $CDCl_3$) δ 7.40 (bs, 5H), 7.08 (bs, 1H), 5.27-4.84 (m, 2H), 4.73-4.07 (m, 2H), 3.81-3.00 (m, 6H), 2.57-1.60 (m, 8H), 1.25 (bs, 28H), 0.85 (t, J=5.8 Hz, 3H). MS (ESI+) m/z 592.69; calcd for $C_{34}H_{55}N_3O_4Na$ (MNa$^+$): 592.41.

RS-33-7:
(S)-benzyl-2-((S)-2-(pentadecylcarbamoyl)pyrrolidine-1-carbonyl)pyrrolidine-1-carboxylate. From pentadecylamine (66%) $^1$H NMR (400 MHz, $CDCl_3$) δ 7.36-7.30 (bs, 5H), 7.10 (bs, 1H), 5.25-4.91 (m, 2H), 4.65-4.13 (m, 2H), 3.78-3.03 (m, 6H), 2.58-1.81 (m, 8H), 1.25 (bs, 26H), 0.88 (t, J=6.7 Hz, 3H). MS (ESI+) m/z 578.3; calcd for $C_{33}H_{53}N_3O_4Na$ (MNa$^+$): 578.39.

RS-33-8:
(S)-benzyl 2-((S)-2-((2-methoxy-5-(trifluoromethyl)phenyl) carbamoyl)pyrrolidine-1-carbonyl)pyrrolidine-1-carboxylate. From 2-methoxy-5-(trifluoromethyl)aniline. (35%); $^1$H NMR (400 MHz, $CDCl_3$) δ 9.22 (bd, 1H), 8.66 (dd, J=12.8, 1.4 Hz, 1H), 7.87-7.03 (m, 6H), 6.87 (dd, J=8.5, 3.1 Hz, 1H), 5.09 (m, 3H), 4.90-4.37 (m, 2H), 4.02-3.80 (m, 3H), 3.76-3.22 (m, 3H), 2.53-0.77 (m, 8H).

MS (ESI+) m/z 542.24; calcd for $C_{26}H_{28}F_3N_3O_5Na$ (MNa$^+$): 542.19.

RS-33-9:
(S)-benzyl 2-((S)-2-((2-chlorobenzyl)carbamoyl)pyrrolidine-1-carbonyl)pyrrolidine-1-carboxylate. From 2-chlorobenzylamine. (35%); $^1$H NMR (400 MHz, $CDCl_3$) δ 7.65 (bs, 1H), 7.36-7.10 (m, 9H), 5.25-4.88 (m, 2H), 4.78-4.22 (m, 4H), 3.75-3.45 (m, 4H), 2.25-1.75 (m, 8H). MS (ESI+) m/z 492.1; calcd for $C_{25}H_{28}ClN_3O_4Na$ (MNa$^+$): 492.16.

RS-33-10:
(S)-benzyl 2-((S)-2-((2,4-dichlorobenzyl)carbamoyl)pyrrolidine-1-carbonyl) pyrrolidine-1-carboxylate. From 2,4-dichlorobenzylamine. (69%); $^1$H NMR (400 MHz, CDCl$_3$) δ 7.52 (bs, 1H), 7.38-7.17 (m, 8H), 5.26-4.88 (m, 2H), 4.75-4.30 (m, 4H), 3.84-3.17 (m, 4H), 2.26-1.74 (m, 8H). MS (ESI+) m/z 526.26; calcd for $C_{25}H_{27}Cl_2N_3O_4Na$ (MNa$^+$): 526.12.

RS-33-11:
(S)-benzyl 2-((S)-2-((2-(trifluoromethyl)benzyl)carbamoyl) pyrrolidine-1-carbonyl) pyrrolidine-1-carboxylate. From 2-(trifluoromethyl)benzylamine. (73%); $^1$H NMR (400 MHz, CDCl$_3$) δ 7.76-7.07 (m, NH & ArH, 10H), 5.26-4.82 (m, 2H), 4.72-4.25 (m, 4H), 3.79-3.50 (m, 4H), 2.23-1.70 (m, 8H). MS (ESI+) m/z 526.26; calcd for $C_{26}H_{28}F_3N_3O_4Na$ (MNa$^+$): 526.19.

RS-33-12:
(S)-benzyl 2-((S)-2-((4-chlorobenzyl)carbamoyl)pyrrolidine-1-carbonyl)pyrrolidine-1-carboxylate. From 4-chlorobenzylamine (58%); $^1$H NMR (400 MHz, CDCl$_3$) δ 7.46-7.09 (m, 5H), 6.88 (dd, J=16.3, 8.5 Hz, 4H), 5.27-4.23 (m, 4H), 4.10-2.97 (m, 7H), 2.75-1.74 (m, 9H), 1.64-1.07 (m, 3H). MS (ESI+) m/z 492.2; calcd for $C_{25}H_{28}ClN_3O_4Na$ (MNa$^+$): 492.16.

RS-33-13:
(S)-benzyl 2-((S)-2-((2,6-difluorobenzyl)carbamoyl)pyrrolidine-1-carbonyl) pyrrolidine-1-carboxylate. From 2,6-difluorobenzylamine. (38%); $^1$H NMR (400 MHz, CDCl$_3$) δ 7.6 (s, 1H), 7.50-7.08 (m, 6H), 6.87-6.80 (m, 2H), 5.39-4.84 (m, 2H), 4.77-4.40 (m, 4H), 3.90-3.50 (m, 4H), 2.25-1.75 (m, 8H). MS (ESI+) m/z 494.2; calcd for $C_{25}H_{27}F_2N_3O_4Na$ (MNa$^+$): 494.19.

RS-33-14:
(S)-benzyl 2-((S)-2-((3-chlorobenzyl)carbamoyl)pyrrolidine-1-carbonyl)pyrrolidine-1-carboxylate. From 3-chlorobenzylamine. (37%); $^1$H NMR (400 MHz, CDCl$_3$) δ 7.61 (bs, 1H), 7.34-7.02 (m, 9H), 5.25-4.80 (m, 2H), 4.74-4.08 (m, 4H), 3.83-3.17 (m, 4H), 2.65-1.15 (m, 8H). MS (ESI+) m/z 492.2; calcd for $C_{25}H_{28}ClN_3O_4Na$ (MNa$^+$): 492.17.

RS-33-15:
(S)-benzyl 2-((S)-2-((2-methoxybenzyl)carbamoyl)pyrrolidine-1-carbonyl) pyrrolidine-1-carboxylate. From 2-methoxybenzylamine. (60%); $^1$H NMR (400 MHz, CDCl$_3$) δ 7.5-7.10 (m, NH & ArH, 8H), 6.80-6.9 (m, 2H), 5.37-4.89 (m, 2H), 4.77-4.21 (m, 4H), 3.83 (s, 3H), 3.8-3.19 (m, 4H), 2.40-1.75 (m, 8H). MS (ESI+) m/z 488.3; calcd for $C_{26}H_{31}N_3O_5Na$ (MNa$^+$): 488.21.

RS-33-16:
(S)-benzyl 2-((S)-2-((3-methoxybenzyl)carbamoyl)pyrrolidine-1-carbonyl)pyrrolidine-1-carboxylate. From 3-methoxybenzylamine. (69%); $^1$H NMR (400 MHz, CDCl$_3$) δ 7.4 (bs, 1H), 7.35-7.00 (m, 6H), 6.85-6.75 (m, 3H), 5.22-4.78 (m, 2H), 4.73-4.05 (m, 4H), 3.86-3.12 (m, 7H), 2.62-1.31 (m, 8H). MS (ESI+) m/z 488.3; calcd for $C_{26}H_{31}N_3O_5Na$ (MNa$^+$): 488.22.

RS-33-17:
(S)-benzyl 2-((S)-2-((4-bromophenethyl)carbamoyl)pyrrolidine-1-carbonyl) pyrrolidine-1-carboxylate. From 4-bromophenylamine. (74%); $^1$H NMR (400 MHz, CDCl$_3$) δ 7.70 (bs, 1H), 7.48-7.25 (m, 7H), 7.20-7.10 (m, 2H), 5.27-4.86 (m, 2H), 4.55-4.20 (m, 2H), 3.69-3.30 (m, 4H), 2.77-2.70 (m, 2H), 2.5 (m, 2H), 2.21-1.75 (m, 8H). MS (ESI+) m/z 552.2; calcd for $C_{26}H_{30}BrN_3O_4Na$ (MNa$^+$): 550.13.

RS-33-18:
(S)-benzyl 2-((S)-2-(pentylcarbamoyl)pyrrolidine-1-carbonyl)pyrrolidine-1-carboxylate. From n-pentylamine. (oil, 92%); $^1$H NMR (400 MHz, CDCl$_3$) δ 7.36-7.28 (bs, 5H), 7.10 (bs, 1H), 5.30-4.90 (m, 2H), 4.65-4.20 (m, 2H), 3.79-3.50 (m, 4H), 3.45-3.10 (m, 4H), 2.5-1.70 (m, 8H), 1.5 (m, 2H), 1.3 (bs, 2H) 0.87 (t, J=6.8 Hz, 3H). MS (ESI+) m/z 438.3; calcd for $C_{23}H_{33}N_3O_4Na$ (MNa$^+$): 438.24.

RS-33-19:
(S)-benzyl 2-((S)-2-(heptylcarbamoyl)pyrrolidine-1-carbonyl)pyrrolidine-1-carboxylate. From n-heptylamine. (oil, 86%); $^1$H NMR (400 MHz, CDCl$_3$) δ 7.27 (bs, 5H), 7.05 (bs, 1H), 5.22-4.86 (m, 2H), 4.50-4.05 (m, 2H), 3.78-3.01 (m, 6H), 2.20-1.75 (m, 8H), 1.40 (m, 2H), 1.21 (m, 8H), 0.82 (d, J=6.8 Hz, 3H). MS (ESI+) m/z 466.4; calcd for $C_{25}H_{37}N_3O_4Na$ (MNa$^+$): 466.27.

RS-33-20:
(S)-benzyl 2-((S)-2-(dodecylcarbamoyl)pyrrolidine-1-carbonyl)pyrrolidine-1-carboxylate. From n-dodecylamine. (white solid, 81%); m.p. 56-58° C. $^1$H NMR (400 MHz, CDCl$_3$) δ 7.41-7.28 (m, 5H), 7.02 (bs, 1H), 5.31-4.87 (m, 2H), 4.72-4.08 (m, 2H), 3.80-3.42 (m, 3H), 3.44-3.00 (m, 3H), 2.35-1.80 (m, 8H), 1.45 (m, 2H), 1.24 (bs, 18H), 0.87 (t, J=6.0 Hz, 3H). MS (ESI+) m/z 536.4; calcd for $C_{30}H_{47}N_3O_4Na$ (MNa$^+$): 536.35. CHN analysis calculated for $C_{30}H_{47}N_3O_4$. C, 70.14; H, 9.22; N, 8.18. Found C, 70.50; H, 9.26; N, 8.32.

RS-33-22:
(S)-benzyl-2-((S)-2-((3-(2-(2-ethoxyethoxy)ethoxy)propyl) carbamoyl)pyrrolidine-1-carbonyl) pyrrolidine-1-carboxylate. From 3-(2-(2-ethoxyethoxy)ethoxy)propan-1-amine. (69%) $^1$H NMR (500 MHz, CDCl$_3$) δ 7.28-7.19 (m, 5H), 7.00 (bs, 1H), 5.12-4.89 (m, 2H), 4.50-4.13 (m, 2H), 3.56-3.34 (m, 18H), 2.19-1.60 (m, 10H), 1.13 (t, J=7 Hz, 3H). MS (ESI+) m/z 542.2; calcd for $C_{27}H_{41}N_3O_7Na$ (MNa$^+$): 542.28.

RS-33-23:
(S)-benzyl 2-((S)-2-((benzo[d][1,3]dioxol-5-ylmethyl)carbamoyl)pyrrolidine-1-carbonyl)pyrrolidine-1-carboxylate. From benzo[d][1,3]dioxol-5-ylmethanamine. (48%); $^1$H NMR (400 MHz, CDCl$_3$) δ 8.35-7.59 (m, 1H), 7.59-7.05 (m, 6H), 6.97-6.50 (m, 2H), 5.89 (s, 2H), 5.34-4.86 (m, 2H), 4.78-3.99 (m, 4H), 3.94-3.13 (m, 5H), 2.64-1.15 (m, 7H). MS (ESI+) m/z 502.17; calcd for $C_{26}H_{29}N_3O_6Na$ (MNa$^+$): 502.19.

RS-33-24:
(S)-benzyl 2-((S)-2-((3-phenylpropyl)carbamoyl)pyrrolidine-1-carbonyl)pyrrolidine-1-carboxylate. From 3-phenylpropylamine. (32%); MS (ESI+) m/z 486.20; calcd for $C_{27}H_{33}N_3O_4Na$ (MNa$^+$): 486.23.

RS-33-25:
(S)-benzyl 2-((S)-2-(adamantan-1-ylcarbamoyl)pyrrolidine-1-carbonyl)pyrrolidine-1-carboxylate. From adamantan-1-amine. (31%); $^1$H NMR (400 MHz, CDCl$_3$) δ 7.46-7.17 (m, 5H), 6.72 (d, J=13.5 Hz, 1H), 5.36-4.90 (m, 2H), 4.54 (d, J=7.9 Hz, 1H), 4.41 (m, 1H), 3.81-3.19 (m, 3H), 2.52-1.72 (m, 18H), 1.66 (bs, 6H). MS (ESI+) m/z 502.37; calcd for $C_{28}H_{37}N_3O_4Na$ (MNa$^+$): 502.26.

RS-33-27:
(S)-benzyl 2-((S)-2-([1,1'-biphenyl]-4-ylcarbamoyl)pyrrolidine-1-carbonyl) pyrrolidine-1-carboxylate. From [1,1'-biphenyl]-4-amine. (40%); MS (ESI+) m/z 520.22; calcd for $C_{30}H_{31}N_3O_4Na$ (MNa$^+$): 520.22.

RS-33-28:
(S)-benzyl 2-((S)-2-(naphthalen-2-ylcarbamoyl)pyrrolidine-1-carbonyl)pyrrolidine-1-carboxylate. From naphthalen-2-amine. (45%); MS (ESI+) m/z 494.12; calcd for $C_{28}H_{29}N_3O_4Na$ (MNa$^+$): 494.21.

RS-33-29:
(S)-benzyl 2-((S)-2-((3,4-dihydroxyphenethyl)carbamoyl)pyrrolidine-1-carbonyl)pyrrolidine-1-carboxylate. From 4-(2-aminoethyl)benzene-1,2-diol. (35%). MS (ESI+) m/z 504.21; calcd for $C_{26}H_{31}N_3O_6Na$ (MNa+): 504.21.

General Catalytic Hydrogenation Procedure for Synthesis of NH-Pro-Pro-NH-Amide Derivatives (FIG. 2, Scheme 2).

RS-33-21:
(S)—N-dodecyl-1-((S)-pyrrolidine-2-carbonyl)pyrrolidine-2-carboxamide hydrochloride. Compound RS-33-20 (200 mg) was dissolved in $CH_3OH$ (5 mL). THF (2 mL), water (1 mL) and 0.5 N aqueous HCl (200 µL) were added successively followed by addition of Pd—C (10% Pd/C; 40 mg). The reaction was purged under vaccum, and a balloon of $H_2$ gas was used to blanket the reaction while stirring at RT. After 3 hrs the reaction was complete by TLC and MS monitoring. The Pd—C suspension was filtered and the resulting filtrate was evaporated under vacuum. The residue was dissolved in a minimum amount of isopropanol, and a few drops of diethylether bubbled with HCl gas was added dropwise. The precipitate that formed was washed with diethylether, filtered, and subjected to high vaccum to yield RS-33-21 as the hydrochloride salt. (white powder, 80%); mp. 141-144° C.; $^1$H NMR (400 MHz, MeOD) δ 4.58 (dd, J=8.6, 6.5 Hz, 1H), 4.41 (dd, J=8.2, 5.8 Hz, 1H), 3.71 (dt, J=9.6, 6.9 Hz, 1H), 3.58 (dt, J=9.7, 7.0 Hz, 1H), 3.46-3.32 (m, 2H), 3.26-3.08 (m, 2H), 2.60-2.45 (m, 1H), 2.27 (dt, J=15.1, 6.6 Hz, 1H), 2.20-1.83 (m, 6H), 1.59-1.43 (m, 2H), 1.29 (s, 18H), 0.90 (t, J=6.8 Hz, 3H). $^{13}$C NMR (100 MHz, $CD_3OD$) δ 172.39, 166.80, 60.49, 59.05, 47.12, 46.16, 39.02, 31.67, 29.53, 29.39, 29.36, 29.34, 29.31, 29.08, 29.02, 28.96, 28.05, 26.52, 24.63, 23.70, 22.34, 13.05. MS (ESI+) m/z 380.44; calcd for $C_{22}H_{42}N_3O_2$ (MH+): 380.32. CHN analysis calcd for $C_{22}H_{42}ClN_3O_2C$, 63.51; H, 10.18; N, 10.10 found: C, 63.85; H, 10.26; N, 10.07.

RS-33-12a:
(S)—N-(4-chlorobenzyl)-1-((S)-pyrrolidine-2-carbonyl)pyrrolidine-2-carboxamide hydrochloride (60%); MS (ESI+) m/z 336.3; calcd for $C_{17}H_{22}ClN_3O_2$ (MH+): 336.15.

RS-33-13a:
(S)—N-(2,6-difluorobenzyl)-1-((S)-pyrrolidine-2-carbonyl)pyrrolidine-2-carboxamide hydrochloride (64%); $^1$H NMR (500 MHz, $D_2O$) δ 7.24 (m, 1H), 6.88 (t, J=7.6 Hz, 2H), 4.49 (m, 2H), 4.28 (m, 2H), 3.70-3.10 (m, 5H), 2.20-1.72 (m, 6H), 1.18 (m, 2H). MS (ESI+) m/z 338.2; calcd for $C_{17}H_{22}F_2N_3O_2$ (MH+): 338.17.

RS-33-23a:
(S)—N-(benzo[d][1,3]dioxol-5-ylmethyl)-1-((S)-pyrrolidine-2-carbonyl)pyrrolidine-2-carboxamide hydrochloride (50%); $^1$H NMR (400 MHz, MeOD) δ 6.82 (s, 1H), 6.81-6.74 (m, 2H), 5.92 (s, 2H), 4.63 (dd, J=8.6, 6.2 Hz, 1H), 4.49 (dd, J=8.1, 5.9 Hz, 1H), 4.32 (m, 2H), 3.74 (m, 1H), 3.61 (m, 1H), 3.40 (m, 2H), 2.53 (m, 1H), 2.30 (m, 1H), 2.20-1.90 (m, 6H).

RS-33-26:
(S)—N-(adamantan-1-yl)-1-((S)-pyrrolidine-2-carbonyl)pyrrolidine-2-carboxamide hydrochloride. (76%); MS (ESI+) m/z 346.33; calcd for $C_{20}H_{32}N_3O_2$ (MH+): 346.25.

RS-33-27a:
(S)—N-([1,1'-biphenyl]-4-yl)-1-((S)-pyrrolidine-2-carbonyl)pyrrolidine-2-carboxamide hydrochloride. (42%); $^1$H NMR (400 MHz, $D_2O$) δ 7.40 (d, J=8.4 Hz, 2H), 7.12 (dd, J=13.5, 8.1 Hz, 4H), 6.90 (t, J=7.5 Hz, 2H), 6.80 (t, J=7.2 Hz, 1H), 4.51 (dd, J=11.7, 6.4 Hz, 1H), 3.57 (m, 1H), 3.38 (m, 1H), 3.18 (m, 2H), 2.32 (m, 1H), 2.18 (dd, J=12.1, 7.3 Hz, 1H), 1.82 (m, 4H), 1.71 (m, 2H). MS (ESI+) m/z 364.1; calcd for $C_{22}H_{26}N_3O_2$ (MH+): 346.20.

RS-33-28a:
(S)—N-(naphthalen-2-yl)-1-((S)-pyrrolidine-2-carbonyl)pyrrolidine-2-carboxamide hydrochloride (55%); $^1$H NMR (400 MHz, $D_2O$) δ 7.88 (s, 1H), 7.71 (t, J=10.5 Hz, 3H), 7.46-7.28 (m, 3H), 4.54 (m, 2H), 3.62 (m, 1H), 3.49 (m, 1H), 3.32 (bs, 2H), 2.46 (m, 1H), 2.33 (m, 1H), 1.96 (m, 6H). MS (ESI+) m/z 338.27; calcd for $C_{20}H_{24}N_3O_2$ (MH+): 338.19.

RS-33-29a:
(S)—N-(3,4-dihydroxyphenethyl)-1-((S)-pyrrolidine-2-carbonyl)pyrrolidine-2-carboxamide hydrochloride. (35%); $^1$H NMR (400 MHz, MeOD) δ 6.86-6.47 (m, 3H), 4.49 (m, 2H), 3.95-3.20 (m, 10H), 2.79-1.75 (m, 11H).

RS-33-201:
(S)—N-dodecyl-1-((S)-1-(3-phenylpropyl)pyrrolidine-2-carbonyl)pyrrolidine-2-carboxamide hydrochloride. (FIG. 3, Scheme 3). At ambient temperature, a solution of RS-33-21 (15 mg; 0.04 mmol) in dichloromethane (4 mL) and phenylpropyl bromide (8.8 mg; 6.7 µL; 0.044 mmol; 1.1 eq) were mixed and N,N-diisopropylethylamine (Hunigs base; 7.74 mg; 10.43 µL; 0.06 mmol; 1.5 eq) was added. The reaction mixture was stirred for one hour and evaporated under reduced pressure to afford the crude residue which was further purified by silica gel column chromatography to afford RS-33-201 (12 mg, 61%). $^1$H NMR (400 MHz, $CD_3OD$) δ 7.26-7.13 (m, 5H), 4.37 (m, 1H), 3.62 (m, 2H), 3.50 (m, 1H), 3.16 (m, 3H), 2.75-2.35 (m, 4H), 2.30-2.00 (m, 4H), 1.90-1.80 (m, 7H), 1.50 (bs, 2H), 1.28 (bs, 18H), 0.90 (m, 3H). MS (ESI+) m/z 498.27; calcd for $C_{31}H_{52}N_3O_2$ (MH+): 498.41.

General Procedure for Synthesis of RS-40-1 to RS-40-4: Reductive Amination Reactions. (FIG. 4, Scheme 4).

At ambient temperature, a solution of RS-33-21 (free base; 0.082 mmol) in $CHCl_3$ (4 mL) and the respective aldehyde (0.098 mmol) were mixed and solid $NaBH(OAc)_3$ (0.197 mmol) was added. The mixture was stirred for 1 hour and then partitioned between $CHCl_3$ and saturated aqueous sodium bicarbonate. The organic layer was dried over anhydrous sodium sulfate, filtered, and concentrated in vacuo. The residue was purified by silica gel column chromatography affording compounds RS-40-1 to RS-40-4 in 65-78% yield. Several were characterized as their hydrochloride salts.

RS-40-1:
(S)-1-((S)-1-benzylpyrrolidine-2-carbonyl)-N-dodecylpyrrolidine-2-carboxamide hydrochloride. From benzaldehyde. (62%) $^1$H NMR (400 MHz, MeOD) δ 7.56 (d, J=6.6 Hz, 2H), 7.46 (m, 3H), 4.64 (bs, 1H), 4.44 (ABq, $J_{AB}$=13 Hz, 2H), 4.18-3.97 (m, 1H), 3.69 (bs, 1H), 3.56-3.35 (m, 3H), 3.13 (m, 2H), 2.66 (bs, 1H), 2.34-1.94 (m, 5H), 1.94-1.74 (m, 2H), 1.46 (m, 2H), 1.28 (bs, 18H), 0.89 (t, J=6.7 Hz, 3H). MS (ESI+) m/z 470.28; calcd for $C_{29}H_{48}N_3O_2$ (MH+): 470.37.

RS-40-2:
(S)—N-dodecyl-1-((S)-1-(pyridin-4-ylmethyl)pyrrolidine-2-carbonyl)pyrrolidine-2-carboxamide hydrochloride. From isonicotinaldehyde. (62%) $^1$H NMR (400 MHz, MeOD) δ 9.03 (d, J=6.5 Hz, 2H), 8.39 (d, J=6.5 Hz, 2H), 5.0-4.82 (m, 3H), 4.30 (m, 1H), 3.75 (m, 2H), 3.66-3.44 (m, 2H), 3.14 (m, 2H), 2.95-2.66 (m, 1H), 2.48-2.15 (m, 3H), 2.15-1.94 (m, 3H), 1.87 (m, 1H), 1.49 (m, 2H), 1.28 (bs, 18H), 0.89 (t, J=6.8 Hz, 3H). MS (ESI+) m/z 471.29; calcd for $C_{28}H_{47}N_4O_2$ (MH+): 471.36.

RS-40-3:
(S)—N-dodecyl-1-((S)-1-(pyridin-3-ylmethyl)pyrrolidine-2-carbonyl)pyrrolidine-2-carboxamide. From nicotinaldehyde. (60%) $^1$H NMR (400 MHz, $CDCl_3$) δ 8.50 (bs, 2H), 7.77 (d, J=7.6 Hz, 1H), 7.28 (m, 1H), 7.15 (bs, 1H), 4.53 (d, J=7.8 Hz, 1H), 3.90 (d, J=13 Hz, 1H), 3.57 (d, J=13 Hz, 1H), 3.46 (m, 1H), 3.31 (m, 2H), 3.15 (m, 2H), 2.42 (m, 2H), 2.13 (m, 3H), 2.0-1.74 (m, 4H), 1.69 (bs, 1H), 1.44 (m, 2H), 1.24

(bs, 18H), 0.88 (t, J=6.5 Hz, 3H). MS (ESI+) m/z 471.31; calcd for $C_{28}H_{47}N_4O_2$ (MH+): 471.36.

RS-40-4:

(S)—N-dodecyl-1-((S)-1-(pyridin-2-ylmethyl)pyrrolidine-2-carbonyl)pyrrolidine-2-carboxamide. From picolinaldehyde. (59%); $^1$H NMR (400 MHz, CDCl$_3$) δ 8.51 (bd, J=5.0 Hz, 1H), 7.65 (t, J=7.0 Hz, 1H), 7.48 (t, J=8.0 Hz, 1H), 7.31 (m, 1H), 7.16 (bt, J=7 Hz, 1H), 4.51 (d, J=8.0 Hz, 1H), 3.95 (d, J=13 Hz, 1H), 3.75 (d, J=13 Hz, 1H), 3.49 (m, 2H), 3.41 (m, 1H), 3.16 (m, 3H), 2.52 (m, 1H), 2.39 (m, 1H), 2.21-1.60 (m, 8H), 1.45 (m, 1H), 1.24 (bs, 18H), 0.88 (t, J=7 Hz, 3H). MS (ESI+) m/z 471.33; calcd for $C_{28}H_{47}N_4O_2$ (MH+): 471.36.

General Procedure for the Synthesis of N-Sulfonamides (FIG. 5, Scheme 5) General Procedure for RS-43-01 to RS-43-04:

Triethylamine (5.1 mg; 7 µL; 0.05 mmol; 1 eq) and substituted sulfonyl chloride (0.055 mmol; 1.1 eq) were added to a solution of RS-33-21 (19 mg; 0.05 mmol; 1 eq) in dichloromethane (2 mL) at 0° C. The reaction mixture was stirred for one hour while slowly warming the contents to ambient temperature. Then, the solvent was removed under reduced pressure while keeping the temperature of the water-bath between 30-32° C. The residue was purified by silica gel column chromatography (using a mixture of methanol:ethyl acetate varying between 5% to 25%) to afford the final compounds in yields ranging from 50% to 75%.

RS-43-01:

(S)—N-dodecyl-1-((S)-1-tosylpyrrolidine-2-carbonyl)pyrrolidine-2-carboxamide. From p-toluenesulfonylchloride. (75%); MS (ESI+) m/z 556.3; calcd for $C_{29}H_{47}N_3O_4S_1Na$ (MNa+): 556.32.

RS-43-02:

(S)—N-dodecyl-1-((S)-1-((4-(tert-pentyl)phenyl)sulfonyl) pyrrolidine-2-carbonyl) pyrrolidine-2-carboxamide. From 4-(tent-pentyl)benzene-1-sulfonyl chloride. (70%); MS (ESI+) m/z 612.5; calcd for $C_{33}H_{55}N_3O_4S_1Na$ (MNa+): 612.38.

RS-43-03:

(2S)-1-((2S)-1-(((7,7-dimethyl-2-oxobicyclo[2.2.1]heptan-1-yl)methyl)sulfonyl) pyrrolidine-2-carbonyl)-N-dodecylpyrrolidine-2-carboxamide. From camphorsulfonylchloride. (50%); MS (ESI+) m/z 616.6; calcd for $C_{32}H_{55}N_3O_5S_1Na$ (MNa+): 616.38.

RS-43-04:

(S)—N-dodecyl-1-((S)-1-(methylsulfonyl)pyrrolidine-2-carbonyl)pyrrolidine-2-carboxamide. From methanesulfonylchloride. (61%); MS (ESI+) m/z 480.4; calcd for $C_{23}H_{43}N_3O_4S_1Na$ (MNa+): 480.29.

General Procedure for Synthesis of Urea Derivatives (FIG. 6, Scheme 6)

A solution of RS-33-21 (200 mg; 0.527 mmol; 1 eq) and triethylamine (60 mg; 82 µL; 0.58 mmol; 1.1 eq) in dichloromethane (4 mL) was added to a suspension of N,N'-carbonyldiimidazole (CDI, 94 mg, 0.58 mmol; 1.1 eq) in dichloromethane (6 mL) affording a slightly yellow clear solution. The mixture was stirred for 24 hours. Then, the reaction was diluted with dichloromethane (5 mL) and quenched with water (10 mL). The aqueous layer was extracted with dichloromethane (5 mL×3). The combined organic layers were dried using anhydrous sodium sulfate, filtered and concentrated in vacuo to yield the product RS-45-00 ((S)-1-((S)-1-(1H-imidazole-1-carbonyl)pyrrolidine-2-carbonyl)-N-dodecylpyrrolidine-2-carboxamide) as a crystalline white solid (195 mg; 78%). MS (ESI+) m/z 496.11; calcd for $C_{26}H_{43}N_5O_3Na$ (MNa+): 496.33.

Synthesis of RS-45-10:

Methyl iodide (180 mg; 79 µL; 1.3 mmol; 4 eq) was added to a solution of RS-45-00 (150 mg; 0.32 mmol; 1 eq) in anhydrous acetonitrile (8 mL). The mixture was stirred at RT for 30 hrs. The solvent was removed under vacuum to yield corresponding carbamoyl imidazolium salt (RS-45-10) as yellow viscous oil (160 mg; 82%). MS (ESI+) m/z 488.14; calcd for $C_{27}H_{46}N_5O_3$ (MNa+): 488.36.

General Procedure for the Synthesis of RS-45-20 to RS-45-22 (FIG. 6, Scheme 6):

The appropriate primary amine (0.03 mmol; 1 eq) and triethylamine (3.3 mg; 5 µL; 0.03 mmol; 1 eq) was added to a solution of RS-45-10 (20 mg; 0.03 mmol; 1 eq) in dichloromethane (4 mL). The mixture was stirred at RT for 24 hours, then washed with 1.0 N HCl (4 mL×2) and brine (4 mL) respectively. The organic layer was dried under anhydrous sodium sulfate, filtered and concentrated in vacuo to yield corresponding ureas RS-45-20 to RS-45-22 in yields ranging 58% to 62%.

RS-45-20:

(S)—N-benzyl-2-((S)-2-(dodecylcarbamoyl)pyrrolidine-1-carbonyl)pyrrolidine-1-carboxamide. From benzylamine. (62%); $^1$H NMR (500 MHz, CDCl$_3$) δ 8.26 (bs, 1H), 7.32 (bs, 5H), 4.81-4.13 (m, 4H), 3.89-3.02 (m, 6H), 2.64-1.62 (m, 8H), 1.60-1.42 (m, 2H), 1.27 (s, 18H), 0.90 (t, J=6.2 Hz, 3H). MS (ESI+) m/z 535.17; calcd for $C_{30}H_{48}N_4O_3Na$ (MNa+): 535.36.

RS-45-21:

(S)—N-(4-chlorobenzyl)-2-((S)-2-(dodecylcarbamoyl)pyrrolidine-1-carbonyl) pyrrolidine-1-carboxamide. From 4-chlorobenzylamine. (58%); MS (ESI+) m/z 569.09; calcd for $C_{30}H_{47}ClN_3O_3Na$ (MNa+): 569.32.

RS-45-22:

(S)—N-(2,4-dichlorobenzyl)-2-((S)-2-(dodecylcarbamoyl) pyrrolidine-1-carbonyl) pyrrolidine-1-carboxamide. From 2,4-dichlorobenzylamine. (60%); $^1$H NMR (500 MHz, CDCl$_3$) δ 7.29-7.12 (m, 3H), 6.94 (bs, 1H), 4.85 (bs, 1H), 4.51 (m, 2H), 4.26 (m, 2H), 3.69-3.43 (m, 3H), 3.31-3.03 (m, 3H), 2.48-2.28 (m, 2H), 2.12-1.65 (m, 6H), 1.38 (m, 2H), 1.24 (bs, 18H), 0.81 (t, J=6.7 Hz, 3H). MS (ESI+) m/z 603.08; calcd for $C_{30}H_{46}Cl_2N_4O_3Na$ (MNa+): 603.28.

RS-45-30:

(S)-4-methoxyphenyl 2-((S)-2-(dodecylcarbamoyl)pyrrolidine-1-carbonyl) pyrrolidine-1-carboxylate. (FIG. 7, Scheme 7) 4-Methoxyphenol (3.3 mg; 0.0264 mmol; 1.1 eq) and triethylamine (2.5 mg; 2.4 µL; 0.024 mmol; 1 eq) were added to a solution of carbamoylimidazolium salt RS-45-10 (15 mg; 0.024 mmol; 1 eq) in anhydrous acetonitrile (4 mL). The reaction was stirred for 30 hours. The solvent was removed under vacuum and the residue was dissolved in dichloromethane (10 mL) and 0.5 N HCl (5 mL) was added. The aqueous layer was extracted with dichloromethane (5 mL×3). The combined organic layers were washed with water (10 mL) and brine (10 mL) respectively. The organic layer was dried using anhydrous sodium sulfate, filtered, and concentrated under reduced pressure to yield carbamate RS-45-30 (8 mg; 54%). MS (ESI+) m/z 552.54; calcd for $C_{30}H_{47}N_3O_5Na$ (MNa+): 552.34.

RS-61-5:

benzyl((S)-1-((S)-2-(S)-2-(dodecylcarbamoyl)pyrrolidine-1-carbonyl)pyrrolidin-1-yl)-3-(1H-imidazol-4-yl)-1-oxopropan-2-yl)carbamate. (FIG. 8, Scheme 8): Synthesized from RS-33-21 and (S)-2-(benzyloxycarbonylamino)-3-(1H-imidazol-4-yl)propanoic acid using the same condensation reaction conditions listed in FIG. 1A, Scheme 1A and FIG. 1B, Scheme 1B. (50%); MS (ESI+) m/z 651.88; calcd for $C_{36}H_{55}N_6O_5$ (MH+): 651.42.

Synthesis of Proline A-Ring Isosteres (FIG. 9B, Scheme 9):

RS-47-00:

(S)-benzyl 2-(dodecylcarbamoyl)pyrrolidine-1-carboxylate. Commercially available Z-Pro-OH was condensed with n-dodecylamine (Scheme 1 reaction conditions). (96%); m.p. 71-73° C.; $^1$H NMR (400 MHz, CDCl$_3$) δ 7.35 (bs, 5H), 6.69 (bs, 1H), 5.19 (bs, 2H), 4.32 (bs, 1H), 3.51 (bs, 2H), 3.19 (bs, 2H), 2.38 (bs, 1H), 2.17 (bs, 1H), 1.90 (bs, 2H), 1.45 (bs, 2H), 1.25 (bs, 18H), 0.88 (t, J=6.7 Hz, 3H). MS (ESI+) m/z 439.43; calcd for C$_{25}$H$_{40}$N$_2$O$_3$Na (MNa$^+$): 439.29. CHN analysis calculated for C$_{25}$H$_{40}$N$_2$O$_3$. C, 72.08; H, 9.68; N, 6.72. Found C, 72.39; H, 9.83; N, 6.71.

RS-47-01:

(S)—N-dodecylpyrrolidine-2-carboxamide hydrochloride. Compound RS-47-00 was deprotected using catalytic hydrogenation (Scheme 2 reaction conditions) to yield RS-47-01. (80%); m.p. 53-55° C.; $^1$H NMR (400 MHz, CD$_3$OD) δ 4.19 (dd, J=8.3, 7.0 Hz, 1H), 3.38 (m, 2H), 3.24 (td, J=7.0, 3.1 Hz, 2H), 2.42 (m, 1H), 2.10-1.93 (m, 3H), 1.51-1.48 (m, 2H), 1.30 (bs, 18H), 0.90 (t, J=6.8 Hz, 3H). MS (ESI+) m/z 283.34; calcd for C$_{17}$H$_{35}$N$_2$O (MH$^+$): 283.27. CHN analysis calculated for C$_{17}$H$_{35}$ClN$_2$O. C, 64.02; H, 11.06; N, 8.78. Found C, 64.23; H, 11.26; N, 8.71.

RS-47-02:

(S)—N-dodecyl-1-(1H-pyrrole-2-carbonyl)pyrrolidine-2-carboxamide. Synthesized from the condensation reaction of RS-47-01 with pyrrole-2 carboxylic acid (Scheme 1 reaction conditions). (85%) $^1$H NMR (400 MHz, CDCl$_3$) δ 9.85 (bs, 1H), 7.08 (bs, 1H), 6.98 (s, 1H), 6.69 (s, 1H), 6.30 (bs, 1H), 4.80 (d, J=6.3 Hz, 1H), 3.80 (m, 2H), 3.22 (m, 2H), 2.43 (m, 1H), 2.3-1.9 (m, 3H), 1.45 (m, 2H), 1.23 (bs, 18H), 0.86 (t, J=6.5 Hz, 3H); MS (ESI+) m/z 376.26; calcd for C$_{22}$H$_{38}$N$_3$O$_2$ (MH$^+$): 376.29.

RS-47-03:

(S)—N-dodecyl-1-((S)-thiazolidine-4-carbonyl)pyrrolidine-2-carboxamide hydrochloride. Synthesized from the condensation reaction of RS-47-01 with S-thiazoline-2 carboxylic acid. (50%); m.p. 77-79° C.; $^1$H NMR (400 MHz, CD$_3$OD) δ 4.39 (dd, J=8.3, 4.7 Hz, 1H), 4.33 (d, J=9.5 Hz, 1H), 4.00 (m, 2H), 3.79 (m, 1H), 3.68 (m, 1H), 3.25-3.08 (m, 3H), 2.82 (dd, J=10.2, 8.1 Hz, 1H), 2.22-1.92 (m, 4H), 1.49 (m, 2H), 1.29 (bs, 18H), 0.90 (t, J=6.8 Hz, 3H); MS (ESI+) m/z 398.28; calcd for C$_{21}$H$_{41}$N$_3$O$_2$S$_1$ (MH$^+$): 398.28.

RS-47-04:

(S)-1-((R)-2-acetamido-3-mercaptopropanoyl)-N-dodecylpyrrolidine-2-carboxamide Synthesized from the condensation reaction of RS-47-01 with (R)-2-acetamido-3-mercaptopropanoic acid (52%); $^1$H NMR (400 MHz, MeOD) 4.74 (t, J=6.9 Hz, 1H), 4.37 (dd, J=8.2, 4.6 Hz, 1H), 3.84 (m, 2H), 3.17 (m, 2H), 2.90 (dd, J=13.6, 7.3 Hz, 1H), 2.71 (dd, J=13.6, 6.8 Hz, 1H), 2.19 (m, 1H), 2.01 (m, 1H), 1.97 (s, 3H), 1.73 (m, 1H), 1.49 (m, 2H), 1.29 (m, 18H), 0.90 (t, J=6.8 Hz, 3H). MS (ESI+) m/z 450.43; calcd for C$_{22}$H$_{41}$N$_3$O$_3$SNa (MNa$^+$): 450.28.

RS-47-05:

(S)—N-dodecyl-1-((S)-1,2,3,4-tetrahydroisoquinoline-3-carbonyl)pyrrolidine-2-carboxamide hydrochloride. Synthesized from the condensation reaction of RS-47-01 with (S)-1,2,3,4-tetrahydroisoquinoline-3-carboxylic acid (53%); MS (ESI+) m/z 442.24; calcd for C$_{27}$H$_{44}$N$_3$O$_2$ (MH$^+$): 442.34.

RS-47-06:

(S)-1-((S)-azetidine-2-carbonyl)-N-dodecylpyrrolidine-2-carboxamide hydrochloride. Synthesized from the condensation reaction of RS-47-01 with (S)-1-(tert-butoxycarbonyl)azetidine-2-carboxylic acid and subsequent deprotection with trifluoroacetic acid in dichloromethane (1:1). Conversion to the hydrochloride salt was accomplished by treatment with a solution of HCl/diethylether to a solution of the product amine in isopropanol. Subsequent evaporation of the solvent followed by triturating with isopropanol/diethylether afforded the product RS-47-06 (54%); m.p. 150-152° C.; $^1$H NMR (400 MHz, CD$_3$OD) δ 5.27 (t, J=8.7 Hz, 1H), 4.41 (dd, J=8.2, 5.1 Hz, 1H), 4.12 (m, 1H), 3.92 (m, 1H), 3.51 (m, 1H), 3.40 (m, 1H), 3.25 (m, 2H), 2.90 (m, 1H), 2.72 (m, 1H), 2.24 (m, 1H), 2.08 (m, 1H), 1.92 (m, 2H), 1.52 (m, 2H), 1.29 (bs, 18H), 0.90 (t, J=6.8 Hz, 3H). MS (ESI+) m/z 366.45; calcd for C$_{21}$H$_{40}$N$_3$O$_2$ (MH$^+$): 366.31. CHN analysis calculated for C$_{21}$H$_{40}$ClN$_3$O$_2$. C, 62.74; H, 10.03; N, 10.45. Found C, 62.60; H, 10.17; N, 10.38.

Synthesis of Proline B-Ring Isosteres (FIG. 10B, Scheme 10):

Compound RS-48-00 (Synthesized from the standard condensation reaction between n-dodecylamine and (S)-1-(tert-butoxycarbonyl)azetidine-2-carboxylic acid) was treated with a 1:1 solution of CF$_3$COOH and CH$_2$Cl$_2$ (10.0 mL) and stirred at ambient temperature for 2 hours. The solution was evaporated to dryness, the residue dissolved in CH$_2$Cl$_2$, and basified with an aqueous solution of sodium carbonate. Extraction followed by drying over sodium sulfate and evaporation of the solvent yielded the crude residue, which was dissolved in methanol and subjected to treatment with HCl-diethyl ether to yield RS-48-01 as the hydrochloride salt. Treatment of RS-48-01 in separate condensation reactions with Z-Pro-OH or (S)-1-(tert-butoxycarbonyl)azetidine-2-carboxylic acid yielded RS-48-02 and RS-48-04 respectively, which were purified and directly subjected to deprotection reactions. Deprotection of the N-CBz group of RS-48-02 was accomplished using standard catalytic hydrogenation conditions and conversion to the HCl salt yielded the final product RS-48-03. Similarly, removal of the N-Boc group of RS-48-04 was accomplished with trifluoroacetic acid in dichloromethane (1:1), and conversion to the HCl salt yielded the final product RS-48-05.

RS-48-01:

(S)—N-dodecylazetidine-2-carboxamide hydrochloride. (78%); m.p. 103-106° C.; $^1$H NMR (400 MHz, CD$_3$OD) δ 4.98 (t, J=10.1 Hz, 1H), 4.12 (dd, J=18.1, 9.0 Hz 1H), 3.94 (td, J=10.1, 6.1 Hz, 1H), 3.25 (t, J=7.1 Hz, 2H), 2.81 (m, 1H), 2.51 (m, 1H), 1.53 (m, 2H), 1.30 (bs, 18H), 0.89 (t, J=6.8 Hz, 3H). MS (ESI+) m/z 269.42; calcd for C$_{16}$H$_{33}$N$_2$O (MH$^+$): 269.26. CHN analysis calculated for C$_{16}$H$_{33}$ClN$_2$O: C, 63.03; H, 10.91; N, 9.19. Found C, 63.85; H, 11.23; N, 9.24.

RS-48-02:

(S)-benzyl 2-((S)-2-(dodecylcarbamoyl)azetidine-1-carbonyl)pyrrolidine-1-carboxylate. (68%); MS (ESI+) m/z 522.64; calcd for C$_{29}$H$_{45}$N$_3$O$_4$Na (MNa$^+$): 522.33.

RS-48-03:

(S)—N-dodecyl-1-((S)-pyrrolidine-2-carbonyl)azetidine-2-carboxamide hydrochloride. (54%); major rotamer: $^1$H NMR (400 MHz, CD$_3$OD) δ 4.79 (dd, J=9.2, 5.6 Hz, 1H), 4.39 (dd, J=7.8, 7.3 Hz, 1H), 4.25 (m, 2H), 3.35 (m, 2H), 3.20 (m, 2H), 2.64 (m, 1H), 2.43 (m, 1H), 2.30 (m, 1H), 2.08 (m, 3H), 1.51 (m, 2H), 1.29 (bs, 18H), 0.89 (t, J=6.7 Hz, 3H). MS (ESI+) m/z 366.60; calcd for C$_{21}$H$_{40}$N$_3$O$_2$ ((MH$^+$): 366.31.

RS-48-04:

(S)-tent-butyl 2-((S)-2-(dodecylcarbamoyl)azetidine-1-carbonyl)azetidine-1-carboxylate. MS (ESI+) m/z 366.60; calcd for C$_{21}$H$_{40}$N$_3$O$_2$(MH$^+$): 366.31.

RS-48-05:

(S)-1-((S)-azetidine-2-carbonyl)-N-dodecylazetidine-2-carboxamide hydrochloride. (52%); m.p. 109-111° C.; $^1$H NMR (400 MHz, CD$_3$OD) δ 5.14 (t, J=8.7 Hz, 1H), 4.91 (m, 1H), 4.79 (dd, J=9.2, 5.6 Hz, 1H), 4.17-4.00 (m, 3H), 3.94 (m, 1H), 3.22 (m, 2H), 2.85-2.60 (m, 3H), 2.27 (m, 1H), 1.54 (m, 2H), 1.31 (bs, 18H), 0.90 (t, J=6.8 Hz, 3H). MS (ESI+) m/z 352.58; calcd for $C_{20}H_{38}N_3O_2(MH^+)$: 352.30.

Synthesis of Z-Pro-GABA-NH amides (FIG. 11, Scheme 11):

Z-Pro-OH (3 g; 12 mmol; 1 eq) and N-hydroxysuccinimide (1.38 g; 12 mmol; 1 eq) were dissolved in 1,4-dioxane (25 mL) and dicyclohexylcarbodiimide (2.47 g; 12 mmol; 1 eq) was added with rapid stirring. The mixture was stirred overnight at room temperature and the solid urea biproduct was filtered off. The solvent was removed and the oily residue was recrystallized from isopropanol. Crystals of Z-Pro-N-succinimide ester [(S)-1-benzyl 2-(2,5-dioxopyrrolidin-1-yl) pyrrolidine-1,2-dicarboxylate] formed with scratching weighing 3.6 g (yield: 86%; mp. 87-89° C.). Z-Pro-N-succinimide ester (2 g; 5.78 mmol; 1 eq) in acetonitrile (30 mL) was added to a solution of γ-Amino butyric acid (GABA; 600 mg; 5.78 mmol; 1 eq) and triethylamine (750 mg) in a water-acetonitrile mixture (10 mL:10 mL) at RT. After stirring for 20 hours, the solvent was removed under reduced pressure, and the residue was dissolved in a mixed solvent system of 1N HCl (20 mL) and ethyl acetate (50 mL). The organic layer was separated, washed with brine and extracted with 5% aqueous NaHCO$_3$ (30 mL×3). The extract was washed with ethyl acetate (30 mL×3) and the organic portion was washed with brine (30 mL), dried over anhydrous sodium sulfate and the solvent evaporated under reduced pressure. The oily residue thus obtained was triturated with petroleum ether. The crystalline white powder was recrystallized from solvent mixture of ethyl acetate:diethyl ether (60:40) to give pure Z-Pro-NH-GABA [(S)-4-(1-(benzyloxycarbonyl)pyrrolidine-2-carboxamido)butanoic acid] in an yield of 1.82 g (94%); mp: 70-75° C. $^1$H NMR (500 MHz, CDCl$_3$) δ 9.18 (s, 1H), 7.26 (m, 5H), 5.14 (m, 2H), 4.53-4.01 (m, 1H), 3.67-2.99 (m, 4H), 2.53-1.54 (m, 7H), 1.24 (m, 2H). MS (ESI+) m/z 357.2; calcd for $C_{17}H_{22}N_2O_5Na$ (MNa$^+$): 357.14.

Z-Pro-NH-GABA was reacted under standard condensation reactions with appropriate amines as described in Scheme 1 conditions to yield RS-37-01 to RS-37-07 (FIG. 11):

dRS-37-01:
(S)-benzyl 2-((4-((2-chlorobenzyl)amino)-4-oxobutyl)carbamoyl)pyrrolidine-1-carboxylate. From 2-chlorobenzylamine. (55%); $^1$H NMR (500 MHz, CDCl$_3$) δ 7.40-7.20 (m, 8H), 7.10-6.85 (m, 2H), 5.09 (m, 2H), 4.49 (m, 2H), 4.27 (bs, 1H), 3.74-3.08 (m, 5H), 2.38-1.55 (m, 8H). MS (ESI+) m/z 480.3; calcd for $C_{24}H_{28}Cl_1N_3O_4Na$ (MNa$^+$): 480.16.

RS-37-02:
(S)-benzyl 2-((4-((3-chlorobenzyl)amino)-4-oxobutyl)carbamoyl)pyrrolidine-1-carboxylate. From 3-chlorobenzylamine. (54%); MS (ESI+) m/z 480.3; calcd for $C_{24}H_{28}Cl_1N_3O_4Na$ (MNa$^+$): 480.16.

RS-37-03:
(S)-benzyl 2-((4-((4-chlorobenzyl)amino)-4-oxobutyl)carbamoyl)pyrrolidine-1-carboxylate. From 4-chlorobenzylamine. (56%); MS (ESI+) m/z 480.2; calcd for $C_{24}H_{28}Cl_1N_3O_4Na$ (MNa$^+$): 480.16.

RS-37-04:
(S)-benzyl 2-((4-((2,4-dichlorobenzyl)amino)-4-oxobutyl)carbamoyl)pyrrolidine-1-carboxylate. From 2,4-dichlorobenzylamine. (61%); MS (ESI+) m/z 514.2; calcd for $C_{24}H_{27}Cl_2N_3O_4Na$ (MNa$^+$): 514.12.

RS-37-05:
(S)-benzyl 2-((4-((3,4-dichlorobenzyl)amino)-4-oxobutyl)carbamoyl)pyrrolidine-1-carboxylate. From 3,4-dichlorobenzylamine. (53%); MS (ESI+) m/z 514.2; calcd for $C_{24}H_{27}Cl_2N_3O_4Na$ (MNa$^+$): 514.13.

RS-37-06:
(S)-benzyl 2-((4-(dodecylamino)-4-oxobutyl)carbamoyl)pyrrolidine-1-carboxylate. From n-dodecylamine. (80%); $^1$H NMR (400 MHz, CDCl$_3$) δ 7.35 (bs, 5H), 6.78 (bs, 1H), 6.24 (bs, 1H), 5.17 (bs, 2H), 4.30 (bs, 1H), 3.52 (m, 2H), 3.22 (m, 4H), 2.35-1.86 (m, 4H), 1.74 (m, 4H), 1.48 (bs, 2H), 1.28 (bs, 18H), 0.88 (t, J=6.7 Hz, 3H). MS (ESI+) m/z 524.54; calcd for $C_{29}H_{47}N_3O_4Na$ (MNa$^+$): 524.35.

RS-37-07:
(S)-benzyl 2-((14-oxo-3,6,9-trioxa-13-azaheptadecan-17-yl)carbamoyl)pyrrolidine-1-carboxylate. From 3-(2-(2-ethoxyethoxy)ethoxy)propan-1-amine. (70%); $^1$H NMR (500 MHz, CDCl$_3$) δ 7.34 (bs, 5H), 7.08 (bs, 1H), 6.92 (bs, 1H), 5.14 (m, 2H), 4.29 (d, J=5.1 Hz, 1H), 3.64-3.48 (m, 14H), 3.35-3.19 (m, 4H), 2.08 (m, 4H), 1.99-1.60 (m, 6H), 1.19 (t, J=7.0 Hz, 3H). MS (ESI+) m/z 530.3; calcd for $C_{26}H_{41}N_3O_7Na$ (MNa$^+$): 530.28.

RS-42-01:
(S)—N-(4-(dodecylamino)-4-oxobutyl)pyrrolidine-2-carboxamide hydrochloride (FIG. 12, Scheme 12): Compound RS-37-06 was reacted under standard catalytic hydrogenation conditions (H$_2$—Pd/C) to afford the product characterized as the hydrochloride salt (88%); $^1$H NMR (400 MHz, D$_2$O) δ 4.34 (t, J=7.2 Hz, 1H), 3.38 (t, J=6.0 Hz, 2H), 3.19 (t, J=6.8 Hz, 2H), 3.08 (t, J=6.9 Hz, 2H), 2.55-2.33 (m, 1H), 2.21 (t, J=7.3 Hz, 2H), 2.10-1.87 (m, 3H), 1.85-1.65 (m, 2H), 1.43 (s, 2H), 1.19 (s, 18H), 0.78 (t, J=6.0 Hz, 3H). MS (ESI+) m/z 368.55 calcd for $C_{22}H_{42}N_3O_2$ (MH+): 368.32.

Standard reductive amination reaction conditions were used to prepare N—R-Pro-GABA-NH-Dodecylamides from RS-42-01 and their respective aldehydes.

RS-42-02:
(S)-1-benzyl-N-(4-(dodecylamino)-4-oxobutyl)pyrrolidine-2-carboxamide. From benzaldehyde. (71%); MS (ESI+) m/z 458.4; calcd for $C_{28}H_{48}N_3O_2$ (MH$^+$): 458.37.

RS-42-03:
(S)—N-(4-(dodecylamino)-4-oxobutyl)-1-(pyridin-4-ylmethyl)pyrrolidine-2-carboxamide hydrochloride. From isonicotinaldehyde. $^1$H NMR (400 MHz, MeOD) δ 9.05 (d, J=6.6 Hz, 2H), 8.41 (d, J=6.6 Hz, 2H), 4.89 (m, 2H), 4.53 (dd, J=8.7, 7.6 Hz, 1H), 3.85 (m, 1H), 3.55 (m, 1H), 3.20 (dt, J=21.1, 7.0 Hz, 4H), 2.70 (dd, J=15.5, 8.9 Hz, 1H), 2.31 (m, 3H), 2.10 (m, 2H), 1.74 (m, 2H), 1.54 (m, 2H), 1.29 (m, 18H), 0.89 (t, J=6.8 Hz, 3H). MS (ESI+) m/z 459.4; calcd for $C_{27}H_{47}N_4O_2$ (MH+) 459.37.

RS-42-04:
(S)—N-(4-(dodecylamino)-4-oxobutyl)-1-(pyridin-3-ylmethyl)pyrrolidine-2-carboxamide hydrochloride. From nicotinaldehyde. $^1$H NMR (400 MHz, MeOD) δ 8.55 (d, J=1.5 Hz, 1H), 8.43 (dd, J=4.9, 1.3 Hz, 1H), 7.90 (d, J=7.9 Hz, 1H), 7.40 (dd, J=7.7, 4.9 Hz, 1H), 3.84 (d, J=13.1 Hz, 1H), 3.68 (d, J=13.1 Hz, 1H), 3.13 (m, 6H), 2.45 (m, 1H), 2.21 (m, 1H), 2.14 (t, 7.4 Hz, 2H), 1.91-1.61 (m, 5H), 1.48 (m, 2H), 1.28 (bs, 18H), 0.89 (t, J=6.8 Hz, 3H); MS (ESI+) m/z 459.3; calcd for $C_{27}H_{47}N_4O_2$ (MH+) 459.37.

RS-42-05:
(S)—N-(4-(dodecylamino)-4-oxobutyl)-1-(pyridin-2-ylmethyl)pyrrolidine-2-carboxamide hydrochloride. From picolinaldehyde. $^1$H NMR (400 MHz, MeOD) δ 8.54 (d, J=4.3 Hz, 1H), 7.82 (dd, J=7.7, 1.7 Hz, 1H), 7.50 (d, J=7.8 Hz, 1H), 7.34 (dd, J=7.0, 5.4 Hz, 1H), 4.06 (d, J=13.4 Hz, 1H), 3.85 (d, J=13.4 Hz, 1H), 3.43 (bs, 1H), 3.30 (m, 5H), 2.61 (m, 1H), 2.28 (m, 1H), 2.16 (t, J=7.5 Hz, 2H), 1.89-1.73 (m, 5H), 1.48 (m, 2H), 1.28 (bs, 18H), 0.89 (t, J=6.8 Hz, 3H). MS (ESI+) m/z 459.4; calcd for $C_{27}H_{47}N_4O_2$ (MH+) 459.37.

RS-61-01:
(S)—N-(4-(dodecylamino)-4-oxobutyl)-1-((1-methyl-1H-imidazol-2-yl)methyl) pyrrolidine-2-carboxamide hydrochloride. From 1-methyl-1H-imidazole-2-carbaldehyde. $^1$H NMR (400 MHz, MeOD) δ 7.73 (d, J=2.0 Hz, 1H), 7.70 (d, J=2.0 Hz, 1H), 4.34 (t, J=8.2 Hz, 1H), 4.06 (s, 3H), 3.66 (m, 1H), 3.40 (m, 1H), 3.19 (m, 4H), 2.62 (m, 1H), 2.22 (m, 3H), 2.01 (m, 2H), 1.78 (m, 2H), 1.50 (bs, 2H), 1.29 (bs, 20H), 0.89 (t, J=6.7 Hz, 3H). MS (ESI+) m/z 462.58; calcd for $C_{26}H_{48}N_3O_2(MH^+)$: 434.37.

Synthesis of N-Sulfonamide-Pro-GABA-NH-dodecylamides (FIG. 13, Scheme 13):
Same reaction conditions used as in FIG. 1A, Scheme 1A and FIG. 1B, Scheme 1B.

RS-44-01:
(S)—N-(4-(dodecylamino)-4-oxobutyl)-1-tosylpyrrolidine-2-carboxamide. From 4-methylbenzene-1-sulfonyl chloride. (52%); $^1$H NMR (500 MHz, CDCl$_3$) δ 7.70 (d, J=8.0 Hz, 2H), 7.30 (d, J=8.0 Hz, 2H), 5.70 (bs, 2H), 4.03 (m, 1H), 3.56 (m, 1H), 3.40 (m, 1H), 3.25-3.07 (m, 4H), 2.36 (m, 6H), 2.10-1.69 (m, 5H), 1.49 (m, 2H), 1.28 (m, 18H), 0.83 (t, J=6.9 Hz, 3H). MS (ESI+) m/z 544.3; calcd for $C_{28}H_{47}N_3O_4SNa$ (MNa$^+$): 544.32.

RS-44-02:
(S)—N-(4-(dodecylamino)-4-oxobutyl)-1-((4-(tert-pentyl)phenyl)sulfonyl)pyrrolidine-2-carboxamide. From 4-tert-pentylbenzene-1-sulfonyl chloride. (78%); MS (ESI+) m/z 600.5; calcd for $C_{32}H_{55}N_3O_4S_1Na$ (MNa$^+$): 600.38.

RS-44-03:
(2S)-1-(((7,7-dimethyl-2-oxobicyclo[2.2.1]heptan-1-yl)methyl)sulfonyl)-N-(4-(dodecylamino)-4-oxobutyl)pyrrolidine-2-carboxamide. From camphorsulfonyl chloride. (53%); MS (ESI+) m/z 604.5; calcd for $C_{31}H_{55}N_3O_5S_1Na$ (MNa$^+$): 604.38.

RS-44-04:
(S)—N-(4-(dodecylamino)-4-oxobutyl)-1-(methylsulfonyl)pyrrolidine-2-carboxamide. From methylsulfonyl chloride. (60%); MS (ESI+) m/z 468.3; calcd for $C_{22}H_{43}N_3O_4S_1Na$ (MNa$^+$): 468.29.

Synthesis of N-Amide-Pro-GABA-NH-dodecylamides (FIG. 14, Scheme 14):
Same reaction conditions used in FIG. 1A, Scheme 1.

RS-61-2:
(S)—N-(4-(dodecylamino)-4-oxobutyl)-1-(1-methyl-1H-imidazole-2-carbonyl) pyrrolidine-2-carboxamide. From 1-methyl-1H-imidazole-2-carboxylic acid. MS (ESI+) m/z 498.65; calcd for $C_{26}H_{45}N_5O_3Na$ (MNa$^+$): 498.34.

RS-61-3:
(S)-1-(3-(1H-benzo[d]imidazol-2-yl)propanoyl)-N-(4-(dodecylamino)-4-oxobutyl) pyrrolidine-2-carboxamide. From 3-(1H-benzo[d]imidazol-2-yl)propanoic acid. (53%); $^1$H NMR (400 MHz, MeOD) δ 7.90 (d, J=8.4 Hz, 1H), 7.75 (m, 2H), 4.33 (m, 1H), 3.72 (m, 1H), 3.44 (m, 2H), 3.25-3.11 (m, 4H), 2.25-2.00 (m, 6H), 1.85-1.70 (m, 2H), 1.48 (m, 2H), 1.39 (m, 4H), 1.29 (m, 18H), 0.91 (t, J=6.0 Hz, 3H). MS (ESI+) m/z 540.78; calcd for $C_{31}H_{50}N_5O_3$ (MH$^+$): 540.39.

RS-61-4:
benzyl((S)-1-(S)-2-((4-(dodecylamino)-4-oxobutyl)carbamoyl)pyrrolidin-1-yl)-3-(1H-imidazol-4-yl)-1-oxopropan-2-yl)carbamate. From (S)-2-(benzyloxycarbonylamino)-3-(1H-imidazol-4-yl)propanoic acid. MS (ESI+) m/z 639.88; calcd for $C_{35}H_{55}N_6O_5$ (MH$^+$): 639.42.

The Effect of PRCP Inhibitors on PK Activation on HPAEC.

Human pulmonary artery endothelial cells (HPAEC) were purchased from Invitrogen (Carlsbad, Calif.) and were cultured as previously described.[20] The cells were grown in Dulbecco's Modified Eagle's Medium (DMEM) overnight in 96 well plates (Costar). Cells were washed gently three times with HEPES-carbonated buffer (137 mM NaCl, 3 mM KCl, 12 mM NaHCO$_3$, 14.7 mM HEPES, 5.5 mM Glucose, 0.1% Gelatin, 2 mM CaCl$_2$, 1 mM MgCl$_2$, 7.1 pH, 37° C.) between each incubation step. Gelatin blocking buffer (1% Gelatin) was prepared by adding appropriate amount of 5% gelatin stock to HEPES-carbonated buffer as described above. In the first step, gelatin blocking buffer was used to reduce the non specific binding. As part of this step, the cells were incubated with 1% gelatin buffer for 1 hour. In second and third steps, the cells were incubated with 20 nM high molecular weight kininogen (HK), and with 20 nM of PK and different concentrations of PRCP inhibitors (1 μM to 3 mM), respectively.

The Effect of PRCP Inhibitors on Recombinant Prolylcarboxypeptidase (rPRCP) Activity.

The effects of the inhibitors of PRCP were determined using a previously published method[31]. Briefly, rPRCP was incubated in the presence or absence of various PRCP inhibitors in HEPES-carbonated buffer containing 1 mM Ala-Pro-paranitroaniline (APpNA, a PRCP chromogenic substrate). The final volume was 100 μL and the time of incubation was 60 min. Negative control had only 1 mM APpNA in HEPES-Carbonated buffer. Generation of free p-nitroaniline from APpNA was determined by monitoring changes in absorbance at 405 nm. Assays were done a minimum of 3 times.

Determination of the Specificity of Compound RS-33-21.

After finding the optimal concentration of α-kallikrein, FXIIa, FXIa, or trypsin to produce a high signal-to-noise ratio, the effects of various concentrations of RS-33-21 on these serine proteases were determined according to published methods. All values were calculated as percentage of positive control after subtraction of background. Briefly, purified human serum was added to 200 μL of substrate buffer solution containing hippuryl-L-arginin in triplicated test tubes. Commercially available pooled normal human serum was used. The tubes were tightly covered, vortexed for 15 seconds and incubated for 60 min at 37° C. in a shaker water bath. The enzymatic reaction was stopped by addition of 250 μL of 1 M HCl solution and vortexed for 15 seconds. The blanks were stopped immediately after the addition of serum by 250 μL of 1M HCl before incubation. All samples were incubated on ice for 5 min. 1500 μL ethyl acetate was added, vortexed for 30 s and centrifuged for 10 min at 4000 g. 1 mL of the upper layer (ethyl acetate) was transferred into a 5 mL test tube and placed in a boiling water bath for 45-60 min to evaporate the ethyl acetate thoroughly, 3 mL of 1M NaCl solution was added to each tube and vortexed for 30 s. All samples were placed in water bath at 70° C. for 5 min to redissolve all the residual hippuric acid, then vortexed for 30 s. After 15 min of incubation at room temperature, the absorbance of hippuric acid was read at λ=228 nm.

The effect of RS-33-21 on the major membrane and plasma carboxypeptidases was determined. The effect of RS-33-21 on subtilisin activity in the reaction was examined with the specific substrate ZAALpNA composed of 0.1 mM ZAALpNA in the 50 mM Tris-HCl/10 mM CaCl$_2$ buffer, pH 8.5. The reaction mixture was incubated at 37° C. for 1 h. The reaction was stopped by the addition of 0.5 M HCl.

Determination of the Effect of RS-33-21 on PRCP-Induced Bradykinin Generation on HPAEC.

HPAEC were incubated with 100 nM HK for 1 h at 37° C., as previously described[32]. After incubation, cells were washed and treated with 100 nM PK in the absence or presence of RS-33-21. Supernatants were collected and either frozen at −70° C. or immediately deproteinized with trichloroacetic acid. BK in the samples was determined using a commercial kit (MARKIT BK, Dainippon Pharmaceutical; Osaka, Japan), performed according to the manufacturer instructions. The metabolites of BK were determined by LC-MS.

The Effect of RS-33-21 on PRCP-Induced Nitric Oxide NO Formation on HPAEC.

HPAEC were treated with 100 nM HK and incubated for 1 h at 37° C. After washing three times with HEPES buffer, cells were then incubated with 100 nM PK in the absence and presence of 100 µM of RS-33-21 for 1 h at 37° C. The solution was collected to measure the amount of nitrate+nitrite (the final products of nitric oxide metabolism) in each sample using a fluorometric assay (Cayman Chemicals, Ann Arbor, Mich.) according to the manufacturer's protocol. The fluorescence was read at an excitation wavelength of 360 nm and an emission wavelength of 460 nm using BioTek Synergy HT Multi-Mode Microplate Reader. Nitrate+nitrite levels in each sample were normalized to that for the buffer alone.

The Effect of RS-33-21 on PRCP-Induced 6-Keto Prostaglandin $F_{1\alpha}$ Release from HPAEC.

HPAEC were treated with 100 nM HK and incubated for 1 h at 37° C. Cells were then incubated with 100 nM PK±30 µM of compound RS-33-21 for 1 h at 37° C. The solution was collected to measure the amount of 6-keto prostaglandin $F_{1\alpha}$ (a stable analog of prostacyclin) in each sample using a competitive acetylcholinesterase (AChE) enzyme immunoassay (Cayman Chemicals, Ann Arbor, Mich.) according to the manufacturer's protocol. The absorbance was measured spectrophotometrically at 405 nm. The data was analyzed using a computer spreadsheet provided on the manufacturer's website. 6-keto prostaglandin $F_{1\alpha}$ level in each sample was normalized to that for the buffer alone.

The Effect of RS-33-21 on HPAEC Permeability Via PRCP-Dependent PK Activation.

The effect of the inhibitors of PRCP on vascular permeability was assessed using an in vitro vascular permeability assay kit (Chemicon/Millipore, Mass.) according to the manufacturer's protocol. Briefly, collagen coating solution in 0.2×PBS, pH 7.1 was added to the inserts. After incubating for 1 h at room temperature, the inserts were hydrated with cell growth medium for 15 min and seeded with 200 µL of cell suspension (1.0×10$^6$ HPAEC/mL). The plate was incubated at 37° C. for 24 h until a cell monolayer was formed. The inserts were then treated with cell basal medium (negative control); 1 µg/mL LPS (positive control); 0.1 µM HK/PK complex in the absence or presence of HOE-140 (1 µM) and lisinopril (1 µM, an angiotensin converting enzyme) and incubated at 37° C. for 18 h. The effect of the RS-33-21 (100 µM) alone and in combination with HK/PK complex (0.1 µM) on endothelial permeability was also studied. The fluorescence was read at an excitation wavelength of 485 nm and an emission wavelength of 528 nm using BioTek Synergy 2 Multi-Mode Microplate Reader.

Effects of RS-33-21 on the Metabolism of Angiotensin II and Bradykinin by rPRCP.

The specificity of RS-33-21 was assessed by LC/MS analysis of the metabolism of angiotensin III (Ang III, Ang$_{2-8}$) to angiotensin 2-7 (Ang$_{1-7}$) and des-Arg$^9$bradykinin (BK$_{1-8}$) to BK$_{1-7}$ by rPRCP, as previously described[33].

Effect of RS-33-21 on Food Intake.

Mice were single housed one week before the experiment. Male mice (n=6 per group; 4 months old) were then food deprived for 24 hours. Thirty minutes before food was re-introduced, mice were injected ip (100 µl total volume) with either saline (vehicle control) or 1, 10, or 100 mg/kg of RS-33-21. Food intake was measured at 1 hour, 2 hours, 4 hours 8 hours and 24 hours.

Mouse Carotid Artery Thrombosis Models.

C57Bl/6 WT mice and C57Bl/6 mice deficient in factor fXII (FXII$^{-/-}$), were used in these studies. The procedures were approved by the Institutional Animal Care and Use Committee of Vanderbilt University. After anesthesia with pentobarbital (50 mg/kg IP), the right common carotid artery was exposed and fitted with a Doppler flow probe (Model 0.5 VB, Transonic System, Ithaca, N.Y.). PBS with or without Compound RS-33-21 (0.8 mg/kg) was infused into the internal jugular vein 15 min before vascular injury in 50 µl volume. Thrombus formation was induced by applying two 1×1.5 mm filter papers (GB003, Schleicher & Schuell, Keene, N.H.) saturated with FeCl$_3$ (3.5% for wild type mice, 12.5% for FXII$^{-/-}$ mice) to opposite sides of the artery for three min. Flow was monitored for 30 min. Mice were sacrificed by pentobarbital overdose after conclusion of the experiment, while under anesthesia.

Statistical Analysis.

Results are expressed as mean±standard error of mean (SEM) of at least three independent experiments each performed in triplicates. Data was analyzed using ANOVA or the $X^2$ test to assess statistical significance of observed differences between drug treated and corresponding control groups. The Tukey-Kramer test was used to adjust for post hoc pairwise comparisons. Two representative concentrations (IC$_{50}$ and absolute inhibition) of RS-33-21 were chosen for statistical analysis of the inhibition studies. RS-33-21 was compared with z-Pro-Pro. For all comparisons, statistical significance was defined as $p<0.05$.

Results

Compound RS-33-21 is a Selective PRCP Inhibitor.

Applicants chose compound RS-33-21 from the library of analogs based on results with the initial chromogenic- and cell-based screening assays, and evaluated its effect on other plasma serine proteases. Compound RS-33-21 inhibited rPRCP in a dose-dependent manner with a K$_i$ value of 43 µM (FIG. 16A), but failed to inhibit α-kallikrein, factor XIIa (FXIIa), factor XIa (FXIa) or trypsin at concentrations >1.0 mM. z-Pro-Prolinal (our lead compound) had a little effect on rPRCP activity at the tested concentrations, FIG. 16A. This finding is consistent with a previously described observation and suggests that z-Pro-Prolinal is a very weak inhibitor of PRCP[31]. For comparison, soybean trypsin inhibitor (SBTI) inhibited α-kallikrein, FXIa, and trypsin with K$_i$ values of 6.15, 0.62, and 0.12 respectively (Table 15), while corn trypsin inhibitor blocked FXIIa with a K$_i$ of 0.12 µM under our experimental conditions. Next, investigations were performed to determine whether RS-33-21 inhibited PRCP-dependent PK activation on endothelium. As shown in FIG. 16B, compound RS-33-21 inhibited the activation of PK to kallikrein in a dose-dependent manner. While z-Pro-Prolinal had a little effect on the production of kallikrein, RS-33-21 markedly reduced the hydrolysis of S2302 by kallikrein produced on HPAEC with K$_i$ values of 34 µM.

Since PRCP is a serine carboxypeptidase, applicants tested the effect of RS-33-21 on other carboxypeptidases. The serine carboxypeptidases CPN[23] and CPM[24] regulate kinin activity through proteolysis of BK, and are mainly involved in regulating chronic inflammation. Compound RS-33-21 did not inhibit metabolism of hippuryl-lysine by CPN (hCPN, partially purified from plasma) or CPM[27,34], while 1,10-phenanthroline blocked CPN and CPM with K$_i$ values of 615.4 and 393.8 µM respectively (Table 15). Carboxypeptidase A (CPA) is a highly conserved protease found in pancreas and mast cell granules. Although its substrate selectivity is different from that of PRCP, both CPA and PRCP cleave the C-terminal aromatic or aliphatic amino acids of proteins or peptides. Carboxypeptidase A [CPA, EC 3.4.17.1] and carboxypeptidase B [CPB, EC 3.4.17.2] were not inhibited by RS-33-21. 1,10-phenanthroline inhibited CPA and CPB with $K_i$ values of 486 and 738.5 ηM, respectively (Table 15).

Ang II[35] and BK[33] are well-established proteolytic targets of PRCP. Previously, applicants described a LC/MS-based method for characterizing Ang II metabolism by rPRCP. This method was used to evaluate the effects of RS-33-21 on PRCP-catalyzed cleavage of Ang II to $Ang_{1-7}$ and $BK_{1-8}$ to $BK_{1-7}$. Compound RS-33-21 (100 µM) effectively blocked both enzymatic reactions (FIGS. 16C and 16D). Further studies with purified rPRCP determined that RS-33-21 was a competitive inhibitor of PRCP (FIG. 16E). These findings suggested that RS-33-21 is a selective inhibitor of PRCP.

Effects of Compound RS-33-21 on PRCP-Mediated Processes In Vitro.

PRCP-dependent PK activation stimulates vascular endothelial cells to produce NO and $PGI_2$ via bradykinin-mediated $B_2$ receptor activation.[28] Applicants initially determined the generation of bradykinin (BK) in the absence or presence of RS-33-21 using a previously described method[32]. PRCP-induced increases in kallikrein and kallikrein-dependent bradykinin were measured in HPAECs. Incubation of HPAECs with the complex of HK/PK caused an increase in BK generation (FIG. 17A). Conversely, RS-33-21 (100 µM) reduced PK activation by PRCP and subsequent BK generation downstream (FIG. 17A). Next, the effect of UM8190 on BK-induced release of NO and $PGI_2$ was determined. Compound RS-33-21 (100 µM) reduced NO and $PGI_2$ production by 80% (FIG. 17B, 17C) for cells on which HK/PK complexes were allowed to assemble. PK activated by PRCP also facilitates BK generation on endothelial cells, with a subsequent increase in cell permeability.[28] Consistent with this, treatment of HPAEC with 0.1 µM alone did not alter cell permeability, while addition of the HK/PK complex (0.1 µM each) resulted in significantly increase permeability (FIG. 17D). In the presence of HK/PK, compound RS-33-21 (100 µM) reduced cell permeability by 90% (FIG. 17D). These results demonstrate the efficacy of RS-33-21 in inhibiting known PRCP-mediated reactions.

Effects of Compound RS-33-21 on Food Intake in Mice.

Investigations were performed to assess the effectiveness and minimum time required for RS-33-21 to reduce food intake. Mice were deprived of food for 24 h prior to being randomly assigned to receive intraperitoneal infusions of RS-33-21 at 1, 10, or 100 mg/kg. Food intake was determined at fixed intervals (1, 2, 4, 8, or 24 h) after drug administration. As shown in FIG. 18, Panel A, administration of RS-33-21 started to attenuate food intake within 1 h. Significant declines in food intake were observed when mice were treated with RS-33-21 at 10 (6 mice per group, P<0.05 vs saline) or 100 mg/kg (6 mice/grop, P<0.05 vs saline, P<0.05 vs 10 mg/kg RS-33-21) at all time intervals (FIG. 18, Panels A through E), with a dose effect clearly apparent. Mice treated with the lowest RS-33-21 dose (1 mg/kg) also had lower food intake, although the reduction was not significant at 2, 4, 8, or 24 h. Zhou and colleagues[22] recently reported on the orixogenic effect of a substituted prolyl-2-benzimidazole PRCP inhibitor in mice. Although the affinity of RS-33-21 for rPRCP is significantly lower than that of the prolyl-2-benzimidazole inhibitor, Compound RS-33-21 (100 mg/kg) was five times more potent at decreasing food intake at a similar dose. Our results are consistent with published studies showing that PRCP inhibition or disruption of the PRCP gene results in reduced food intake and decreased body weight in mice[15]. Cumulatively, the in vitro and in vivo studies demonstrate that RS-33-21 is a potent anorexigenic agent that inhibits PRCP-dependent pathways.

The Antithrombotic Effect of Compound RS-33-21 in Normotensive Mice.

Previously, applicants proposed that PRCP could contribute to thrombin generation and blood clot formation by converting PK to α-kallikrein, promoting the sequential conversion of the protease zymogens factor XII (FXII), factor XI (FXI), and factor IX (FIX) of the intrinsic pathway of blood coagulation to their active forms (FXIIa, FXIa, and FIXa, respectively). As FXII-deficient ($FXII^{-/-}$) mice are resistant to thrombus formation in arterial injury and cerebral ischemia-reperfusion models,[37, 38] applicants postulated that RS-33-21 might have an antithrombotic effect. Compound RS-33-21 was tested in mice with a model in which carotid artery thrombosis is induced by exposing the vessel to varying concentrations of ferric chloride ($FeCl_3$). In wild type C57BL/6 mice (n=5), RS-33-21 (10 mg/kg IV) did not prevent vessel occlusion, nor prolong the time to arterial occlusion, compared to vehicle (PBS) when thrombosis was induced with 3.5% $FeCl_3$ (the lowest concentration that reproducibly causes arterial occlusion in wild type mice).[37, 39] Thrombus formation in this model is dependent on FXII, and it is possible that PK activation through FXIIa, or PK-independent activation of FXII could have overwhelmed any effect of UM8190 on PK activation. To address this concern, applicants tested RS-33-21 on thrombus formation in $FXII^{-/-}$ mice, using 12.5% $FeCl_3$, which causes a high rate of vessel occlusion in these animals.[37] While all $FXII^{-/-}$ control mice treated with PBS (n=5) experienced rapid vessel occlusion with 12.5% $FeCl_3$, 4 of 6 $FXII^{-/-}$ mice treated with RS-33-21 (10 mg/kg IV) did not develop occlusion. These results suggest RS-33-21 has an antithrombotic effect, although the potency is difficult to determine at this point.

DISCUSSION AND CONCLUSIONS

Previous studies on the effects of PRCP inhibition used inhibitors that were either modified peptides[59] or small molecules (aryl imidazoles or benzimidazoles)[22]. These drugs did not penetrate the blood-brain barrier well. Applicants synthesized a class of reversible, potent and selective PRCP inhibitors to address this limitation. Several laboratories, including ours, previously showed that 1-[1-(benzyloxycarbonyl)-L-prolyl]prolinal (Z-Pro-Pro-OH) inhibits PRCP, albeit with a high $IC_{50}$ (>2 mM)[31]. Applicants synthesized a series of Pro-Pro B-ring amide analogs (Z-Pro-Pro-NH amides) and explored several classical isosteric replacements for the proline ring. Applicants discovered the importance of an unsubstituted nitrogen proline Ring A and that activity is enhanced with a dodecyl amide group on proline ring B.

Applicants found that the administration of RS-33-21 induced suppression of appetite, indicating appetite is partially dependent on PRCP in fasted mice. Compound RS-33-21 induced appetite loss that was dose- and time-dependent. Applicants founds that that glucose levels in compound RS-33-21-treated mice were relatively low but not statistically significant compared with control mice (Table 16). Applicants did not observe shortening of carotid artery occlusion times in wild type C57Bl/6 mice treated with RS-33-21, and observed evidence for an antithrombotic effect in FXII deficient mice.

Compound RS-33-21 is a novel synthetic PRCP inhibitor, which has anti-inflammatory, antithrombotic, and food suppressant properties. Compound RS-33-21, and similar compounds discussed in this application may be of great importance in addressing the human epidemic of obesity and diabetes, and associated chronic inflammation.

It is noted that the foregoing examples of the present invention have been provided merely for the purpose of illustration and explanation and are in no way to be construed as limiting of the present invention. While the present invention has been described with reference to an exemplary embodiment, it is understood that the words that have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular embodiments, the present invention is not intended to be limited to the particulars disclosed herein; rather, the present invention extends to all functionally equivalent structures, methods and uses, such as are within the scope of the appended claims.

It is noted that all references, patents and citations which are cited in this document are expressly incorporated herein in their entirety by reference thereto.

REFERENCE LIST

1. Das, U. N.; Rao, A. A. Gene expression profile in obesity and type 2 diabetes mellitus. *Lipids Health Dis.* 2007, 6, 35.
2. Leiter, L. A.; Lewanczuk, R. Z. Of the renin-angiotensin system and reactive oxygen species Type 2 diabetes and angiotensin II inhibition. *Am. J. Hypertens.* 2005, 18, 121-128.
3. Shariat-Madar, B.; Kolte, D.; Verlangieri, A.; Shariat-Madar, Z. Prolylcarboxypeptidase (PRCP) as a new target for obesity treatment. *Diabetes Metab Syndr. Obes.* 2010, 3, 67-78.
4. Brzoska, T.; Luger, T. A.; Maaser, C.; Abels, C.; Bohm, M. Alpha-melanocyte-stimulating hormone and related tripeptides: biochemistry, antiinflammatory and protective effects in vitro and in vivo, and future perspectives for the treatment of immune-mediated inflammatory diseases. *Endocr. Rev.* 2008, 29, 581-602.
5. Luger, T. A.; Schwarz, T.; Kalden, H.; Scholzen, T.; Schwarz, A.; Brzoska, T. Role of epidermal cell-derived alpha-melanocyte stimulating hormone in ultraviolet light mediated local immunosuppression. *Ann. N. Y. Acad. Sci.* 1999, 885, 209-216.
6. Raap, U.; Brzoska, T.; Sohl, S.; Path, G.; Emmel, J.; Herz, U.; Braun, A.; Luger, T.; Renz, H. Alpha-melanocyte-stimulating hormone inhibits allergic airway inflammation. *J. Immunol.* 2003, 171, 353-359.
7. Rossier, J.; Rogers, J.; Shibasaki, T.; Guillemin, R.; Bloom, F. E. Opioid peptides and alpha-melanocyte-stimulating hormone in genetically obese (ob/ob) mice during development. *Proc. Natl. Acad. Sci. U.S.A* 1979, 76, 2077-2080.
8. Shimakura, S.; Miura, T.; Maruyama, K.; Nakamachi, T.; Uchiyama, M.; Kageyama, H.; Shioda, S.; Takahashi, A.; Matsuda, K. Alpha-melanocyte-stimulating hormone mediates melanin-concentrating hormone-induced anorexigenic action in goldfish. *Horm. Behav.* 2008, 53, 323-328.
9. Kim, M. S.; Rossi, M.; Abusnana, S.; Sunter, D.; Morgan, D. G.; Small, C. J.; Edwards, C. M.; Heath, M. M.; Stanley, S. A.; Seal, L. J.; Bhatti, J. R.; Smith, D. M.; Ghatei, M. A.; Bloom, S. R. Hypothalamic localization of the feeding effect of agouti-related peptide and alpha-melanocyte-stimulating hormone. *Diabetes* 2000, 49, 177-182.
10. Costa, J. L.; Hochgeschwender, U.; Brennan, M. The role of melanocyte-stimulating hormone in insulin resistance and type 2 diabetes mellitus. *Treat. Endocrinol.* 2006, 5, 7-13.
11. Hoggard, N.; Rayner, D. V.; Johnston, S. L.; Speakman, J. R. Peripherally administered [Nle4,D-Phe7]-alpha-melanocyte stimulating hormone increases resting metabolic rate, while peripheral agouti-related protein has no effect, in wild type C57BL/6 and ob/ob mice. *J. Mol. Endocrinol.* 2004, 33, 693-703.
12. Huszar, D.; Lynch, C. A.; Fairchild-Huntress, V.; Dunmore, J. H.; Fang, Q.; Berkemeier, L. R.; Gu, W.; Kesterson, R. A.; Boston, B. A.; Cone, R. D.; Smith, F. J.; Campfield, L. A.; Burn, P.; Lee, F. Targeted disruption of the melanocortin-4 receptor results in obesity in mice. *Cell* 1997, 88, 131-141.
13. Dubern, B.; Clement, K.; Pelloux, V.; Froguel, P.; Girardet, J. P.; Guy-Grand, B.; Tounian, P. Mutational analysis of melanocortin-4 receptor, agouti-related protein, and alpha-melanocyte-stimulating hormone genes in severely obese children. *J. Pediatr.* 2001, 139, 204-209.
14. Wirth, M. M.; Olszewski, P. K.; Yu, C.; Levine, A. S.; Giraudo, S. Q. Paraventricular hypothalamic alpha-melanocyte-stimulating hormone and MTII reduce feeding without causing aversive effects. *Peptides* 2001, 22, 129-134.
15. Wallingford, N.; Perroud, B.; Gao, Q.; Coppola, A.; Gyengesi, E.; Liu, Z. W.; Gao, X. B.; Diament, A.; Haus, K. A.; Shariat-Madar, Z.; Mandi, F.; Wardlaw, S. L.; Schmaier, A. H.; Warden, C. H.; Diano, S. Prolylcarboxypeptidase regulates food intake by inactivating alpha-MSH in rodents. *J. Clin. Invest* 2009, 119, 2291-2303.
16. Ngo, M. L.; Mandi, F.; Kolte, D.; Shariat-Madar, Z. Upregulation of prolylcarboxypeptidase (PRCP) in lipopolysaccharide (LPS) treated endothelium promotes inflammation. *J. Inflamm. (Lond)* 2009, 6, 3.
17. Warren, J. B.; Wilson, A. J.; Loi, R. K.; Coughlan, M. L. Opposing roles of cyclic AMP in the vascular control of edema formation. *FASEB J.* 1993, 7, 1394-1400.
18. Zausinger, S.; Lumenta, D. B.; Pruneau, D.; Schmid-Elsaesser, R.; Plesnila, N.; Baethmann, A. Effects of LF 16-0687 Ms, a bradykinin B (2) receptor antagonist, on brain edema formation and tissue damage in a rat model of temporary focal cerebral ischemia. *Brain Res.* 2002, 950, 268-278.
19. Tao, Y. X. The melanocortin-4 receptor: physiology, pharmacology, and pathophysiology. *Endocr. Rev.* 2010, 31, 506-543.
20. Kelly, J. M.; Moir, A. J.; Carlson, K.; Yang, Y.; MacNeil, S.; Haycock, J. W. Immobilized alpha-melanocyte stimulating hormone 10-13 (GKPV) inhibits tumor necrosis factor-alpha stimulated NF-kappaB activity. *Peptides* 2006, 27, 431-437.
21. Ichiyama, T.; Sakai, T.; Catania, A.; Barsh, G. S.; Furukawa, S.; Lipton, J. M. Systemically administered alpha-melanocyte-stimulating peptides inhibit NF-kappaB activation in experimental brain inflammation. *Brain Res.* 1999, 836, 31-37.
22. Zhou, C.; Garcia-Calvo, M.; Pinto, S.; Lombardo, M.; Feng, Z.; Bender, K.; Pryor, K. D.; Bhatt, U. R.; Chabin, R. M.; Geissler, W. M.; Shen, Z.; Tong, X.; Zhang, Z.; Wong, K. K.; Roy, R. S.; Chapman, K. T.; Yang, L.; Xiong, Y. Design and synthesis of prolylcarboxypeptidase (PrCP) inhibitors to validate PrCP as a potential target for obesity. *J. Med. Chem.* 2010, 53, 7251-7263.

23. Erdos, E. G.; SLOANE, E. M. An enzyme in human blood plasma that inactivates bradykinin and kallidins. *Biochem. Pharmacol.* 1962, 11, 585-592.
24. Deddish, P. A.; Skidgel, R. A.; Kriho, V. B.; Li, X. Y.; Becker, R. P.; Erdos, E. G. Carboxypeptidase M in Madin-Darby canine kidney cells. Evidence that carboxypeptidase M has a phosphatidylinositol glycan anchor. *J. Biol. Chem.* 1990, 265, 15083-15089.
25. Couture, R.; Harrisson, M.; Vianna, R. M.; Cloutier, F. Kinin receptors in pain and inflammation. *Eur. J. Pharmacol.* 2001, 429, 161-176.
26. Schatteman, K.; Goossens, F.; Leurs, J.; Verkerk, R.; Scharpe, S.; Michiels, J. J.; Hendriks, D. Carboxypeptidase U at the interface between coagulation and fibrinolysis. *Clin. Appl. Thromb. Hemost.* 2001, 7, 93-101.
27. Schatteman, K. A.; Goossens, F. J.; Scharpe, S. S.; Hendriks, D. F. Activation of plasma procarboxypeptidase U in different mammalian species points to a conserved pathway of inhibition of fibrinolysis. *Thromb. Haemost.* 1999, 82, 1718-1721.
28. Ngo, M. L.; Mandi, F.; Kolte, D.; Shariat-Madar, Z. Upregulation of prolylcarboxypeptidase (PRCP) in lipopolysaccharide (LPS) treated endothelium promotes inflammation. *J. Inflamm. (Lond)* 2009, 6, 3.
29. Mallela, J.; Yang, J.; Shariat-Madar, Z. Prolylcarboxypeptidase: a cardioprotective enzyme. *Int. J. Biochem. Cell Biol.* 2009, 41, 477-481.
30. Chiao, H.; Kohda, Y.; McLeroy, P.; Craig, L.; Housini, I.; Star, R. A. Alpha-melanocyte-stimulating hormone protects against renal injury after ischemia in mice and rats. *J. Clin. Invest* 1997, 99, 1165-1172.
31. Moreira, C. R.; Schmaier, A. H.; Mandi, F.; da, M. G.; Nader, H. B.; Shariat-Madar, Z. Identification of prolylcarboxypeptidase as the cell matrix-associated prekallikrein activator. *FEBS Lett.* 2002, 523, 167-170.
32. Zhao, Y.; Qiu, Q.; Mandi, F.; Shariat-Madar, Z.; Rojkjaer, R.; Schmaier, A. H. Assembly and activation of HK-PK complex on endothelial cells results in bradykinin liberation and NO formation. *Am. J. Physiol Heart Circ. Physiol* 2001, 280, H1821-H1829.
33. Chajkowski, S. M.; Mallela, J.; Watson, D. E.; Wang, J.; McCurdy, C. R.; Rimoldi, J. M.; Shariat-Madar, Z. Highly selective hydrolysis of kinins by recombinant prolylcarboxypeptidase. *Biochem. Biophys. Res. Commun.* 2010.
34. Schatteman, K.; Goossens, F.; Leurs, J.; Verkerk, R.; Scharpe, S.; Michiels, J. J.; Hendriks, D. Carboxypeptidase U at the interface between coagulation and fibrinolysis. *Clin. Appl. Thromb. Hemost.* 2001, 7, 93-101.
35. Mallela, J.; Perkins, R.; Yang, J.; Pedigo, S.; Rimoldi, J. M.; Shariat-Madar, Z. The functional importance of the N-terminal region of human prolylcarboxypeptidase. *Biochem. Biophys. Res. Commun.* 2008, 374, 635-640.
36. Shu, I. W.; Lindenberg, D. L.; Mizuno, T. M.; Roberts, J. L.; Mobbs, C. V. The fatty acid synthase inhibitor cerulenin and feeding, like leptin, activate hypothalamic proopiomelanocortin (POMC) neurons. *Brain Res.* 2003, 985, 1-12.
37. Cheng, Q.; Tucker, E. I.; Pine, M. S.; Sisler, I.; Matafonov, A.; Sun, M. F.; White-Adams, T. C.; Smith, S. A.; Hanson, S. R.; McCarty, 0. J.; Renne, T.; Gruber, A.; Gailani, D. A role for factor XIIa-mediated factor XI activation in thrombus formation in vivo. *Blood* 2010, 116, 3981-3989.
38. Renne, T.; Pozgajova, M.; Gruner, S.; Schuh, K.; Pauer, H. U.; Burfeind, P.; Gailani, D.; Nieswandt, B. Defective thrombus formation in mice lacking coagulation factor XII. *J. Exp. Med.* 2005, 202, 271-281.
39. Wang, X.; Smith, P. L.; Hsu, M. Y.; Gailani, D.; Schumacher, W. A.; Ogletree, M. L.; Seiffert, D. A. Effects of factor XI deficiency on ferric chloride-induced vena cava thrombosis in mice. *J Thromb. Haemost.* 2006, 4, 1982-1988.
40. Jackman, H. L.; Tan, F.; Schraufhagel, D.; Dragovic, T.; Derso, B.; Becker, R. P.; Erdos, E. G. Plasma membrane-bound and lysosomal peptidases in human alveolar macrophages. *Am. J Respir. Cell Mol. Biol.* 1995, 13, 196-204.
41. Kumamoto, K.; Stewart, T. A.; Johnson, A. R.; Erdos, E. G. Prolylcarboxypeptidase (angiotensinase C) in human lung and cultured cells. *J. Clin. Invest* 1981, 67, 210-215.
42. Shariat-Madar, Z.; Mandi, F.; Schmaier, A. H. Identification and characterization of prolylcarboxypeptidase as an endothelial cell prekallikrein activator. *J Biol. Chem.* 2002, 277, 17962-17969.
43. Shariat-Madar, Z.; Mandi, F.; Schmaier, A. H. Recombinant prolylcarboxypeptidase activates plasma prekallikrein. *Blood* 2004, 103, 4554-4561.
44. Wuepper, K. D.; Cochrane, C. G. Plasma prekallikrein: isolation, characterization, and mechanism of activation. *J Exp. Med* 1972, 135, 1-20.
45. Tan, F.; Morris, P. W.; Skidgel, R. A.; Erdos, E. G. Sequencing and cloning of human prolylcarboxypeptidase (angiotensinase C). Similarity to both serine carboxypeptidase and prolylendopeptidase families. *J. Biol. Chem.* 1993, 268, 16631-16638.
46. Wang, L.; Feng, Y.; Zhang, Y.; Zhou, H.; Jiang, S.; Niu, T.; Wei, L. J.; Xu, X.; Xu, X.; Wang, X. Prolylcarboxypeptidase gene, chronic hypertension, and risk of preeclampsia. *Am. J. Obstet. Gynecol.* 2006, 195, 162-171.
47. Zhang, Y.; Hong, X. M.; Xing, H. X.; Li, J. P.; Huo, Y.; Xu, X. P. E112D polymorphism in the prolylcarboxypeptidase gene is associated with blood pressure response to benazepril in Chinese hypertensive patients. *Chin Med J (Engl)* 2009, 122, 2461-2465.
48. Zhu, L.; Carretero, O. A.; Liao, T. D.; Harding, P.; Li, H.; Sumners, C.; Yang, X. P. Role of prolylcarboxypeptidase in angiotensin II type 2 receptor-mediated bradykinin release in mouse coronary artery endothelial cells. *Hypertension* 2010, 56, 384-390.
49. Diano, S. New aspects of melanocortin signaling: a role for PRCP in alpha-MSH degradation. *Front Neuroendocrinol.* 2011, 32, 70-83.
50. Catania, A.; Delgado, R.; Airaghi, L.; Cutuli, M.; Garofalo, L.; Carlin, A.; Demitri, M. T.; Lipton, J. M. alpha-MSH in systemic inflammation. Central and peripheral actions. *Ann. N Y. Acad. Sci.* 1999, 885, 183-187.
51. Caruso, C.; Mohn, C.; Karara, A. L.; Rettori, V.; Watanobe, H.; Schioth, H. B.; Seilicovich, A.; Lasaga, M. Alpha-melanocyte-stimulating hormone through melanocortin-4 receptor inhibits nitric oxide synthase and cyclooxygenase expression in the hypothalamus of male rats. *Neuroendocrinology* 2004, 79, 278-286.
52. Dong, Y.; Cao, J.; Wang, H.; Zhang, J.; Zhu, Z.; Bai, R.; Hao, H.; He, X.; Fan, R.; Dong, C. Nitric oxide enhances the sensitivity of alpaca melanocytes to respond to alpha-melanocyte-stimulating hormone by up-regulating melanocortin-1 receptor. *Biochem. Biophys. Res. Commun.* 2010, 396, 849-853.
53. Catania, A.; Lipton, J. M. The neuropeptide alpha-melanocyte-stimulating hormone: a key component of neuroimmunomodulation. *Neuroimmunomodulation.* 1994, 1, 93-99.
54. Hartmeyer, M.; Scholzen, T.; Becher, E.; Bhardwaj, R. S.; Schwarz, T.; Luger, T. A. Human dermal microvascular endothelial cells express the melanocortin receptor type 1 and produce increased levels of IL-8 upon stimulation with alpha-melanocyte-stimulating hormone. *J. Immunol.* 1997, 159, 1930-1937.

55. Wong, K. Y.; Rajora, N.; Boccoli, G.; Catania, A.; Lipton, J. M. A potential mechanism of local anti-inflammatory action of alpha-melanocyte-stimulating hormone within the brain: modulation of tumor necrosis factor-alpha production by human astrocytic cells. *Neuroimmunomodulation.* 1997, 4, 37-41.

56. Star, R. A.; Rajora, N.; Huang, J.; Stock, R. C.; Catania, A.; Lipton, J. M. Evidence of autocrine modulation of macrophage nitric oxide synthase by alpha-melanocyte-stimulating hormone. *Proc. Natl. Acad. Sci. U.S.A* 1995, 92, 8016-8020.

57. Huszar, D.; Lynch, C. A.; Fairchild-Huntress, V.; Dunmore, J. H.; Fang, Q.; Berkemeier, L. R.; Gu, W.; Kesterson, R. A.; Boston, B. A.; Cone, R. D.; Smith, F. J.; Campfield, L. A.; Burn, P.; Lee, F. Targeted disruption of the melanocortin-4 receptor results in obesity in mice. *Cell* 1997, 88, 131-141.

58. Hill, C.; Dunbar, J. C. The effects of acute and chronic alpha melanocyte stimulating hormone (alphaMSH) on cardiovascular dynamics in conscious rats. *Peptides* 2002, 23, 1625-1630.

59. Yoshimoto, T.; Kawahara, K.; Matsubara, F.; Kado, K.; Tsuru, D. Comparison of inhibitory effects of prolinal-containing peptide derivatives on prolyl endopeptidases from bovine brain and Flavobacterium. *J Biochem.* 1985, 98, 975-979.

60. Shiratori, K.; Ohgami, K.; Ilieva, I. B.; Koyama, Y.; Yoshida, K.; Ohno, S Inhibition of endotoxin-induced uveitis and potentiation of cyclooxygenase-2 protein expression by alpha-melanocyte-stimulating hormone. *Invest Ophthalmol. Vis. Sci.* 2004, 45, 159-164.

61. Hoene, M.; Weigert, C. The role of interleukin-6 in insulin resistance, body fat distribution and energy balance. *Obes. Rev.* 2008, 9, 20-29.

62. Mayerle, J. A novel role for leucocytes in determining the severity of acute pancreatitis. *Gut* 2009, 58, 1440-1441.

63. Chen, X.; Ji, B.; Han, B.; Ernst, S. A.; Simeone, D.; Logsdon, C. D. NF-kappaB activation in pancreas induces pancreatic and systemic inflammatory response. *Gastroenterology* 2002, 122, 448-457.

64. Adams G. N; Zhou Y; Larusch G; Nieman M; Hoit B; Jacobs G; Yu X; Mandi F; Shariat-Madar Z; Okada Y.; Schmaier A. H. Prolylcarboxypeptidase murine hypomorphs are hypertensive and prothrombotic. Journal of Thrombosis and Haemostasis 7 Supplement 2, XXII ISTH Congress, Abstract OC-MO-128. 2009. Ref Type: Abstract 65. Witherow, F. N.; Dawson, P.; Ludlam, C. A.; Webb, D. J.; Fox, K. A.; Newby, D. E. Bradykinin receptor antagonism and endothelial tissue plasminogen activator release in humans. *Arterioscler. Thromb. Vasc. Biol.* 2003, 23, 1667-1670.

66. Revenko, A. S.; Gao, D.; Crosby, J. R.; Bhattacharjee, G.; Zhao, C.; May, C.; Gailani, D.; Monia, B. P.; Macleod, A. R. Selective depletion of plasma prekallikrein or coagulation factor XII inhibits thrombosis in mice without increased risk of bleeding. *Blood* 2011.

67. Ma, L.; Fogo, A. B. Role of angiotensin II in glomerular injury. *Semin. Nephrol.* 2001, 21, 544-553.

We claim:
1. A compound, wherein the compound is:

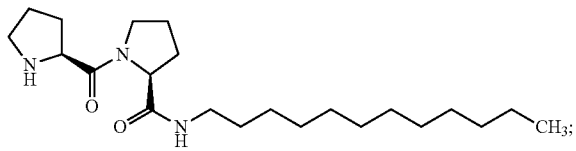

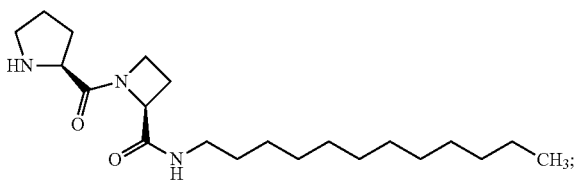

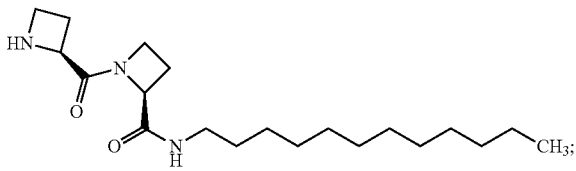

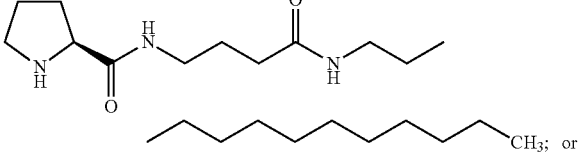

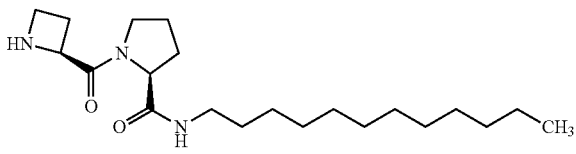

or isosteres or salts thereof.

2. The A pharmaceutical composition comprising a compound of claim 1, wherein the compound is:

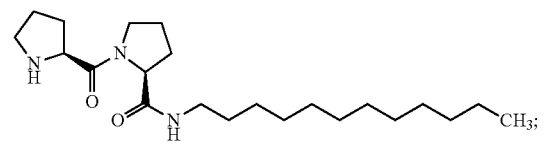

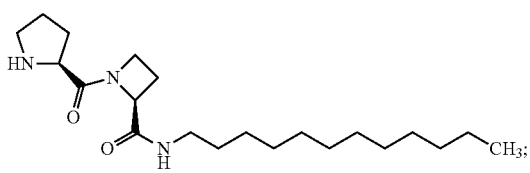

-continued

RS-48-05
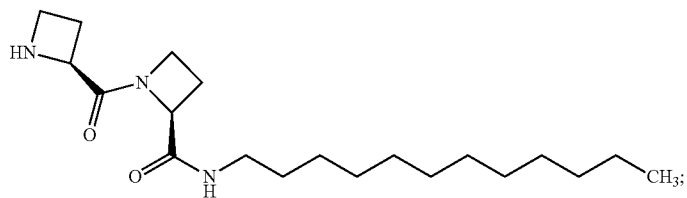

RS-42-01
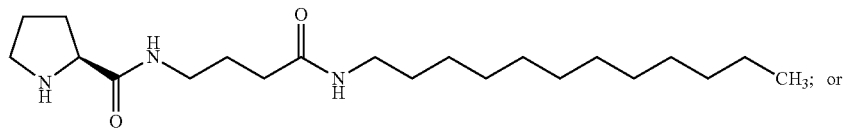

RS-47-06
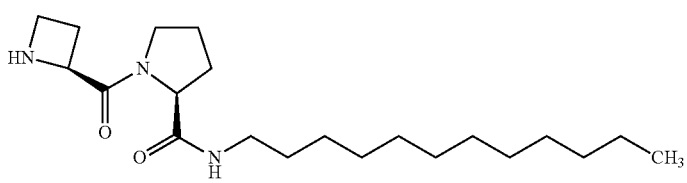

or isosteres or salts thereof and a pharmaceutically acceptable carrier.

3. A method of treating a subject in need of anorexigenic and anti-inflammatory treatment comprising administering to the subject in need of the treatment an effective amount of at least one compound or an isostere or salt thereof according to claim 1, wherein the compound is:

RS-33-21
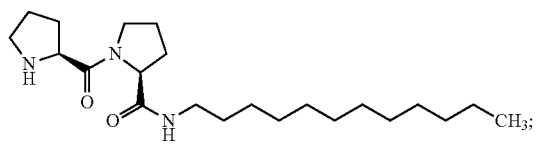

RS-48-03
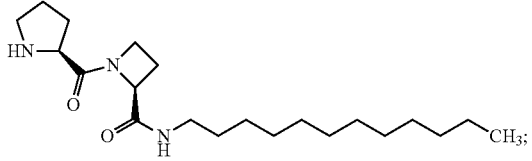

RS-48-05
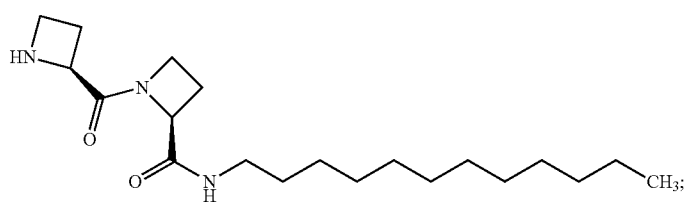

RS-42-01
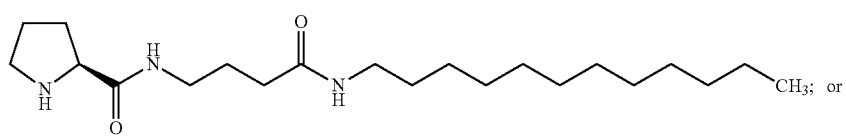

RS-47-06
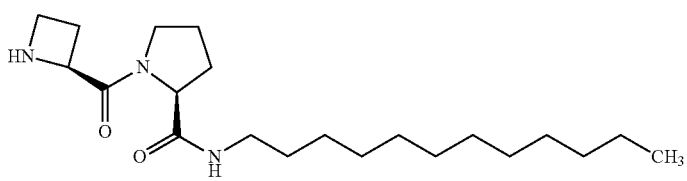

or isosteres or salts thereof.

4. An anorexigenic and anti-inflammatory composition comprising at least one compound according to claim 1 or an isostere or salt thereof, wherein the compound is:

RS-33-21
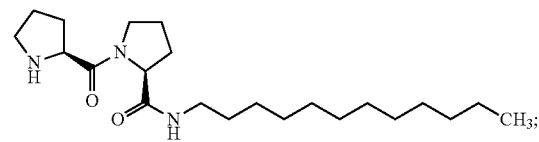

RS-48-03
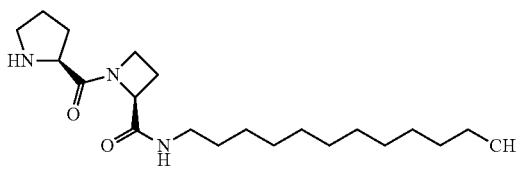

RS-48-05
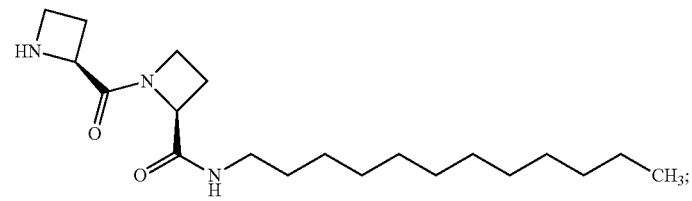

RS-42-01
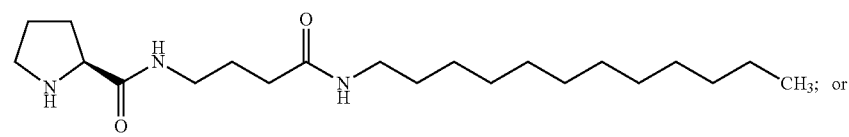

RS-47-06
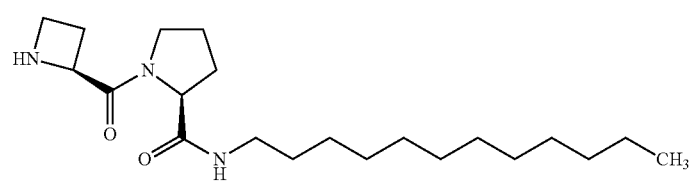

or isosteres or salts thereof.

5. A method of treating obesity comprising administering to a subject in need of the treatment an effective amount of at least one compound according to claim 1 or an isostere or salt thereof, wherein the compound is:

RS-33-21
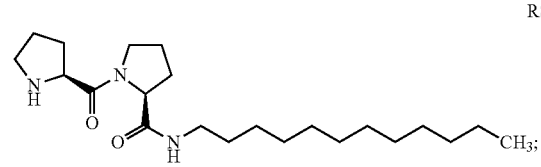

RS-48-03
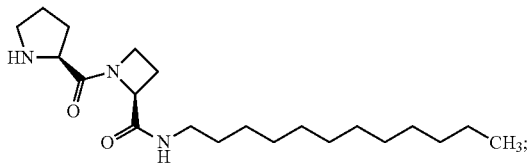

RS-48-05
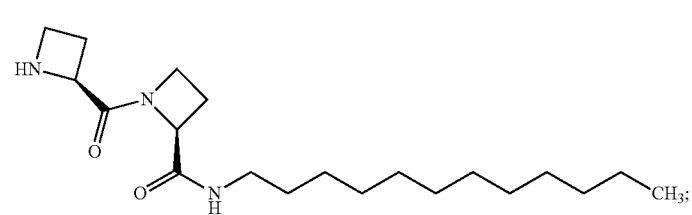

RS-42-01
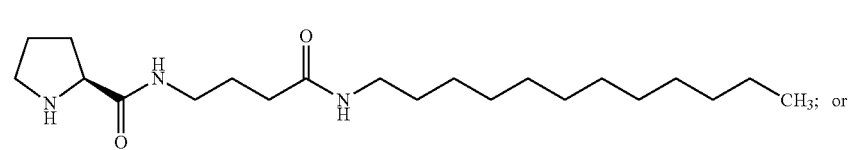

RS-47-06
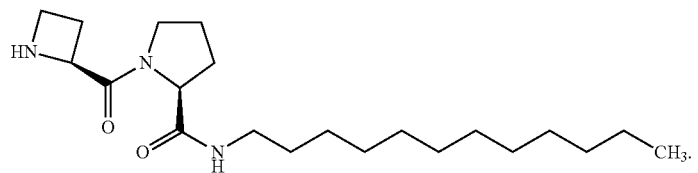
* * * * *